US010245122B2

(12) United States Patent
Way et al.

(10) Patent No.: US 10,245,122 B2
(45) Date of Patent: *Apr. 2, 2019

(54) METHOD AND DEVICE FOR CAUSING TOOTH MOVEMENT

(71) Applicant: ADVANCED ORTHODONTICS AND EDUCATION ASSOCIATION, LLC, Ossining, NY (US)

(72) Inventors: Bryce A. Way, San Jose, CA (US); Christopher U. Phan, San Leandro, CA (US); Dana Leigh Gelman Keiles, Mt. Kisco, NY (US); Richard Johnson, Briarcliff Manor, NY (US); Phillip Abatelli, Wesbury, NY (US)

(73) Assignee: Advanced Orthodontics and Education Association, LLC, Ossining, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,634

(22) Filed: Jul. 7, 2017

(65) Prior Publication Data
US 2017/0304029 A1 Oct. 26, 2017

Related U.S. Application Data

(63) Continuation of application No. 15/208,401, filed on Jul. 12, 2016, now Pat. No. 9,814,547, which is a
(Continued)

(51) Int. Cl.
*A61C 8/00* (2006.01)
*A61C 7/02* (2006.01)
(Continued)

(52) U.S. Cl.
CPC ........ *A61C 8/0096* (2013.01); *A61B 17/1604* (2013.01); *A61B 17/1673* (2013.01);
(Continued)

(58) Field of Classification Search
CPC .... A61C 3/02; A61B 17/1604; A61B 17/1673
See application file for complete search history.

(56) References Cited

U.S. PATENT DOCUMENTS

| 430,299 A | * | 6/1890 | Rand | ........................ | B26F 1/32 |
| | | | | | 30/366 |
| D88,859 S | | 1/1933 | Curtis | | |

(Continued)

FOREIGN PATENT DOCUMENTS

| CA | 2406986 A1 | 4/2004 |
| CN | 2209958 Y | 10/1995 |

(Continued)

OTHER PUBLICATIONS

Adachi et al; Enhancement of cytokine production by macrophages stimulated with (1→3)-beta-D-glucan, grifolan (GRN), isolated from Grifola frondosa; Biol Pharm Bull; 17(12):1554-60; Dec. 1994.

(Continued)

*Primary Examiner* — Ralph A Lewis
(74) *Attorney, Agent, or Firm* — Finnegan, Henderson, Farabow, Garrett & Dunner, L.L.P.

(57) ABSTRACT

A method of increasing movement of a tooth in a jaw having at least one tooth with an orthodontic brace thereon includes: (1) holding a handle of a device, the device having an elongate member extending from the handle and a screw tip at a distal end of the elongate member; (2) moving a sleeve along the elongate member to set a length of exposed screw tip; (3) locking the sleeve in place relative to the screw tip; (4) drilling a hole with the screw tip through a cortical bone of a jaw to increase movement of the tooth; and (5) stopping the drilling when the length of exposed screw tip has penetrated the jaw.

19 Claims, 18 Drawing Sheets

US 10,245,122 B2

Page 2

Related U.S. Application Data continuation of application No. 14/326,069, filed on Jul. 8, 2014, now Pat. No. 9,387,051, which is a continuation of application No. 14/073,778, filed on Nov. 6, 2013, now Pat. No. 8,770,969, which is a continuation of application No. 13/471,099, filed on May 14, 2012, now Pat. No. 8,602,777.

(60) Provisional application No. 61/486,038, filed on May 13, 2011.

(51) Int. Cl.
| A61C 3/02 | (2006.01) |
|---|---|
| A61C 1/08 | (2006.01) |
| A61B 17/16 | (2006.01) |
| A61C 19/04 | (2006.01) |
| A61C 7/12 | (2006.01) |
| A61B 17/00 | (2006.01) |
| A61B 17/56 | (2006.01) |
| A61B 90/00 | (2016.01) |

(52) U.S. Cl.
CPC .......... *A61C 1/082* (2013.01); *A61C 3/02* (2013.01); *A61C 7/02* (2013.01); *A61C 7/12* (2013.01); *A61C 8/0089* (2013.01); *A61C 19/04* (2013.01); *A61B 2017/0046* (2013.01); *A61B 2017/00128* (2013.01); *A61B 2017/1648* (2013.01); *A61B 2017/561* (2013.01); *A61B 2090/062* (2016.02); *A61B 2090/065* (2016.02); *A61C 1/084* (2013.01)

(56) References Cited

U.S. PATENT DOCUMENTS

| | | | |
|---|---|---|---|
| 2,390,309 A | 12/1945 | Keys | |
| 2,564,356 A | 8/1951 | Dianda | |
| 3,360,861 A | 1/1968 | Hoffman | |
| 3,682,177 A | 8/1972 | Ames et al. | |
| 3,838,517 A | 10/1974 | Michnick | |
| 4,123,844 A | 11/1978 | Kurz | |
| 4,347,054 A | 8/1982 | Kraus et al. | |
| D266,109 S | 9/1982 | Sertich et al. | |
| 4,354,832 A | 10/1982 | Wallshein | |
| 4,433,956 A | 2/1984 | Witzig | |
| 4,482,318 A | 11/1984 | Foerster | |
| 4,483,674 A | 11/1984 | Schuetz | |
| 4,549,538 A | 10/1985 | Schadrack et al. | |
| D285,835 S | 9/1986 | Hanses | |
| 4,747,824 A | 5/1988 | Spinello | |
| 4,777,852 A | 10/1988 | Herman et al. | |
| 4,828,113 A | 5/1989 | Friedland et al. | |
| 4,944,677 A | 7/1990 | Alexandre | |
| 5,002,485 A | 3/1991 | Aagesen | |
| 5,030,098 A | 7/1991 | Branford | |
| 5,173,050 A | 12/1992 | Dillon | |
| 5,188,531 A | 2/1993 | Von Sutfin | |
| 5,191,880 A | 3/1993 | McLeod et al. | |
| 5,281,133 A | 1/1994 | Farzin-Nia | |
| 5,320,532 A | 6/1994 | Farzin-Nia et al. | |
| 5,343,883 A | 9/1994 | Murayama | |
| 5,351,404 A | 10/1994 | Smith | |
| 5,439,377 A | 8/1995 | Milanovich | |
| 5,472,344 A | 12/1995 | Binder et al. | |
| 5,547,657 A | 8/1996 | Singleton et al. | |
| D379,750 S | 6/1997 | Thompson et al. | |
| 5,676,682 A * | 10/1997 | Yoon | A61B 10/0233 604/264 |
| 5,957,946 A | 9/1999 | Shuler et al. | |
| 5,961,535 A | 10/1999 | Rosenberg et al. | |
| 6,019,776 A * | 2/2000 | Preissman | A61B 17/3472 600/567 |
| 6,032,677 A | 3/2000 | Blechman et al. | |
| 6,106,289 A | 8/2000 | Rainey et al. | |
| 6,109,916 A * | 8/2000 | Wilcko | A61C 7/00 433/24 |
| D440,479 S | 4/2001 | Hsiao | |
| 6,234,975 B1 | 5/2001 | McLeod et al. | |
| D454,767 S | 3/2002 | Edwards | |
| 6,543,315 B2 | 4/2003 | Huang | |
| 6,592,368 B1 | 7/2003 | Weathers, Jr. | |
| 6,648,639 B2 | 11/2003 | Mao | |
| 6,652,473 B2 | 11/2003 | Kaufman et al. | |
| 6,739,872 B1 | 5/2004 | Turri | |
| 7,166,067 B2 | 1/2007 | Talish et al. | |
| D547,868 S | 7/2007 | Nakanishi | |
| 7,258,694 B1 * | 8/2007 | Choi | A61B 17/32053 606/174 |
| 7,322,948 B2 | 1/2008 | Talish et al. | |
| 7,329,121 B2 | 2/2008 | De Clerck | |
| 7,329,122 B1 * | 2/2008 | Scott | A61C 1/084 433/18 |
| 7,338,494 B2 | 3/2008 | Ryan | |
| 7,347,687 B2 | 3/2008 | Minoretti et al. | |
| 7,419,680 B2 | 9/2008 | LeGeros | |
| 7,462,158 B2 | 12/2008 | Mor | |
| 7,611,355 B2 | 11/2009 | Murias | |
| 7,618,450 B2 | 11/2009 | Zarowski et al. | |
| D607,300 S | 1/2010 | Lin | |
| D616,278 S | 5/2010 | Deguglimo et al. | |
| D628,697 S | 12/2010 | Murias | |
| D629,102 S | 12/2010 | Murias et al. | |
| D644,910 S | 9/2011 | Hsu | |
| D662,206 S | 6/2012 | Way et al. | |
| D668,339 S | 10/2012 | Luoto | |
| 8,602,777 B2 * | 12/2013 | Way | A61C 7/02 433/141 |
| D700,330 S | 2/2014 | Way et al. | |
| 8,770,969 B2 * | 7/2014 | Way | A61C 7/02 433/3 |
| 9,131,992 B2 | 9/2015 | Itsuki et al. | |
| D761,963 S | 7/2016 | Way et al. | |
| 9,387,051 B2 * | 7/2016 | Way | A61C 7/02 |
| 2006/0116581 A1 | 6/2006 | Zdeblick et al. | |
| 2006/0281040 A1 | 12/2006 | Kelling | |
| 2007/0298375 A1 | 12/2007 | Hirsch et al. | |
| 2008/0227046 A1 | 9/2008 | Lowe et al. | |
| 2008/0233541 A1 | 9/2008 | De Vreese et al. | |
| 2009/0035727 A1 | 2/2009 | Maissami | |
| 2009/0042159 A1 | 2/2009 | Yamamoto et al. | |
| 2009/0061375 A1 | 3/2009 | Yamamoto et al. | |
| 2009/0061379 A1 | 3/2009 | Yamamoto et al. | |
| 2009/0061380 A1 | 3/2009 | Yamamoto et al. | |
| 2009/0068285 A1 | 3/2009 | LeGeros et al. | |
| 2009/0275954 A1 | 11/2009 | Phan et al. | |
| 2009/0326602 A1 | 12/2009 | Glukhovsky et al. | |
| 2010/0055634 A1 | 3/2010 | Spaulding et al. | |
| 2010/0092916 A1 | 4/2010 | Teixeira et al. | |
| 2010/0136504 A1 | 6/2010 | Sabilla | |
| 2010/0266983 A1 | 10/2010 | Ng et al. | |
| 2011/0045435 A1 | 2/2011 | Goodman | |
| 2011/0065060 A1 * | 3/2011 | Teixeira | A61C 3/00 433/24 |
| 2011/0207075 A1 | 8/2011 | Altshuler et al. | |
| 2012/0094246 A1 | 4/2012 | Pavlin | |
| 2012/0179070 A1 | 7/2012 | Pommer et al. | |
| 2012/0322018 A1 | 12/2012 | Lowe et al. | |
| 2015/0320523 A1 | 11/2015 | Way et al. | |

FOREIGN PATENT DOCUMENTS

| | | |
|---|---|---|
| CN | 2266999 Y | 11/1997 |
| CN | 1359277 A | 7/2002 |
| CN | 1371663 A | 10/2002 |
| CN | 101262831 A | 9/2008 |
| CN | 201179118 Y | 1/2009 |
| CN | 201200485 Y | 3/2009 |
| CN | 202028800 U | 11/2011 |
| CN | 202113173 U | 1/2012 |
| CN | 202277392 U | 6/2012 |
| CN | 202843827 U | 4/2013 |

(56) References Cited

FOREIGN PATENT DOCUMENTS

| CN | 103249372 A | 8/2013 |
|---|---|---|
| EP | 0531950 A1 | 3/1993 |
| EP | 1535586 A2 | 6/2005 |
| JP | 2007097987 A | 4/2007 |
| JP | 2009000412 A | 1/2009 |
| JP | 2009000412 A | 1/2009 |
| KR | 20030066288 A | 8/2003 |
| RU | 223056 C2 | 2/2004 |
| RU | 2223056 C2 | 2/2004 |
| WO | WO 2006/070957 A1 | 7/2006 |
| WO | WO 2007/047983 A2 | 4/2007 |
| WO | WO 2007/140579 A1 | 12/2007 |
| WO | WO 2009/088165 A1 | 7/2009 |
| WO | WO 2012/158625 A1 | 11/2012 |

OTHER PUBLICATIONS

Alhashimi et al; Orthodontic movement induces high number of cells expressing IFN-gamma at mRNA and protein levels; J Interferon Cytokine Res; 20(1):7-12; Jan. 2000.
Anholm et al; Corticotomy-facilitated orthodontics; CDA J; 14(12):7-11; Dec. 1986.
Arend et al; IL-1, IL-18, and IL-33 families of cytokines; Immunol Rev; 223:20-38; Jun. 2008.
Arias et al; Aspirin, acetaminophen, and ibuprofen: their effects on orthodontic tooth movement; Am J Orthod Dentofacial Orthop; 130(3):364-370; Sep. 2006.
Bai et al.; Interleukin-18 gene polymorphisms and haplotypes in patients with oral lichen planus: a study in an ethnic Chinese cohort; Tissue Antigens; 70(5):390-397Nov. 2007.
Basaran et al.; Interleukins 2, 6, and 8 levels in human gingival sulcus during orthodontic treatment; Am J Orthod Dentofacial Orthop; 130(1):7.e1-6; Jul. 2006.
Bishara et al.; Maxillary expansion: clinical implications; 91(1):3-14; Jan. 1987.
Bolander; Regulation of fracture repair by growth factors; Proc Soc Exp Biol Med; 200(2):165-170; Jun. 1992.
Bossú et al.; Interleukin 18 gene polymorphisms predict risk and outcome of Alzheimer's disease; J Neurol Neurosurg Psychiatry; 78(8):807-877; Aug. 2007 (Author's Manuscript).
Busti et al.; Effects of perioperative anti-inflammatory and immunomodulating therapy on surgical sound healing; Pharmacotherapy; 25(11):1566-1591; Nov. 2005.
Chao et al.; Effects of prostaglandin E2 on alveolar bone resorption during orthodontic tooth movement; Acta Anat (Basel); 132(4):304-309; Jul. 1988.
Chung et al.; Corticotomy-assisted orthodontics; J Clin Orthod; 35(5):331-339; May 2001.
Davidovitch et al.; Neurotransmitters, cytokines, and the control of alveolar bone remodeling in orthodontics; Dent Clin North Am; 32(3):411-435; Jul. 1988.
De Sá et al.; Immunolocalization of interleukin 4, interleukin 6, and lymphotoxin alpha in dental granulomas; Oral Surg Oral Med Oral Pathol Oral Radiol Endod; 96:3356-60; Sep. 2003.
Dienz et al.; The effects of IL-6 on CD4 T cell responses; Clin Immunol; 130(1):27-33; Jan. 2009 (Author's Manuscript).
Erben; Embedding of bone samples in methylmethacrylate: an improved method suitable for bone histomorphometry, histochemistry, and immunohistochemistry; J Histochem Cytochem; 45(2):307-313; Feb. 1997.
Fischer; Orthodontic treatment acceleration with corticotomy-assisted exposure of palatally impacted canines; Angle Orthod; 77(3):417-420; May 2007.
Foster; Principals of removable appliance treatment; in A Textbook of Orthodontics; $2^{nd}$ Ed.; Blackwell Sci. Pub.; Chap. 13; pp. 246-261; Nov. 1975.
Frost; A Synchronous Group of Mammalian Cells Whose In Vivo Behavior Can Be Studied; H Ford Hosp Med Bull; 13:161-172; Jun. 1965.
Frost; Part 1. The biology of fracture healing. An overview for clinicians; Clin Orthop Relat Res; 248:283-293; Nov. 1989.
Frost; Part II. The biology of fracture healing. An overview for clinicians; Clin Orthop Relat Res; 248:294-309; Nov. 1989.
Frost; The regional acceleratory phenomenon: A review; H Ford Hosp Med J; 31(1):3-9; (year of pub. sufficiently earlier than effective US filed and any foreign priority date) 1983.
Gantes et al.; Effects on the periodontium following corticotomy-facilitated orthodontics. Case reports; J Periodonton; 61(4):234-238; Apr. 1990.
Garlet et al.; Cytokine expression pattern in compression and tension sides of the periodontal ligament during orthodontic tooth movement in humans; Eur J Oral Sci; 115(5):355-62; Oct. 2007.
Germec et al.; Lower incisor retraction with a modified corticotomy; Angle Orthod; 76(5):882-890; Sep. 2006.
Glantschnig et al.; M-CSF, TNFalpha and RANK ligand promote osteoclast survival by signaling through mTOR/S6 kinase; Cell Death Differ; 10(10):1165-77; Oct. 2003.
Han et al.; TGFbeta1 selectively up-regulates CCR1 expression in primary murine astrocytes; Glia; 30(1):1-10; Mar. 2000.
Handelman; Nonsurgical rapid maxillary alveolar expansion in adults: a clinical evaluation; Angle Orthod; 67(4):291-305; Aug. 1997.
Haruyama et al.; Estrous-cycle-dependent variation in orthodontic tooth movement; J Dent Res; 81(6):406-410; Jun. 2002.
Hinton et al.; Upper airway pressures during breathing: a comparison of normal and nasally incompetent subjects with modeling studies; Am J Orthod; 89(6);492-498; Jun. 1986.
Hwang et al.; Intrusion of overerupted molars by corticotomy and magnets; Am J Orthod Dentofacial Orthop; 120(2):209-216; Aug. 2001.
Iino et al.; Acceleration of orthodontic tooth movement by alveolar corticotomy in the dog; Am J Orthod Dentofacial Orthop; 131(4):448.e1-e8; Apr. 2007.
Ito et al.; Augmentation of type I IL-1receptor expression and IL-1 signaling by IL-6 and glucocorticoid in murine hepatocytes; J Immunol; 162(7):4260-4265; Apr. 1, 1999.
Jager et al.; Soluble cytokine receptor treatment in experimental orthodontic tooth movement in the rat; Eur J Orthod; 27(1):1-11; Feb. 2005.
Jang et al.; Interleukin-18 gene polymorphisms in Korean patients with Behcet's disease; Clin Exp Rheumatol; 23(4 Suppl 38):559-63; Jul.-Aug. 2005.
Kao et al.; Up-regulation of CC chemokine ligand 20 expression in human airway epithelium by IL-17 through a JAK-independent by MEK/NF-kappaB-dependent signaling pathway; J Immunol; 175(10):6676-6685; Nov. 15, 2005.
Kawasaki et al.; Effects of aging on RANKL and OPG levels in gingival crevicular fluid during orthodontic tooth movement; Orthod Craniofac Res; 9(3):137-142; Aug. 2006.
Khapli et al.; IL-3 acts directly on osteoclast precursors and irreversibly inhibits receptor activator of NF-kappa B ligand-induced osteoclast differentiation by diverting the cells to macrophage lineage; J Immunol; 171(1):142-151; Jul. 2003.
Khoo et al.; Accelerated Orthodontic Treatment; Dentista Y Pacienta; Mexican Dental Journal; Feb. 2011 edition; 11 pages total.
King et al; Later orthodontic appliance reactivation stimulates immediate appearance of osteoclasts and linear tooth movement; Am J Orthod Dentofacial Orthop; 114(6):692-697; Dec. 1998.
King et al.; Measuring dental drift and orthodontic tooth movement in response to various initial forces in adult rats; Am J Orthod Dentofacial Orthop; 99(5):456-465; May 1991.
Kitaura et al.; An anti-c-Fms antibody inhibits orthodontic tooth movement; J Dent Res; 87(4):396-400; Apr. 2008.
Knupfer et al.; sIL-6R: more than an agonist?; Immunol Cell Biol; 86(1):87-91; Jan. 2008.
Kole; Surgical operations on the alveolar ridge to correct occlusal abnormalities; Oral Surg Oral Med Oral Pathol; 12(5):515-529; May 1959.
Krishnan et al.; Cellular, molecular, and tissue-level reactions to orthodontic force; Am J Orthod Dentofacial Orthop; 129(4):469.e1-469.e32; Apr. 2006.

(56) References Cited

OTHER PUBLICATIONS

Krishnan et al.; On a path to unfolding the biological mechanisms of orthodontic tooth movement; J Dent Res; 88(7):597-608; Jul. 2009.
Lean et al.; CCL9/MIP-1gamma and its receptor CCR1 are the major chemokine ligand/receptor species expressed by osteoclasts; J Cell Biochem; 87(4):386-393; Sep. 2002.
Leng et al.; Interleukin-11; Int J Biochem Cell Biol; 29(8-9):1059-1062; Aug.-Sep. 1997.
Liou et al.; Rapid orthodontic tooth movement into newly distracted bone after mandibular distraction osteogenesis in a canine model; Am J Orthod Dentofacial Orthop; 117(4):391-398; Apr. 2000.
Luster; Chemokines—chemotactic cytokines that mediate inflammation; N Engl J Med; 338(7):436-445; Feb. 12, 1998.
McNamara et al.; Orthodontic and Orthopedic Treatment in the Mixed Dentition; Needham Press; pp. 131-144; Jun. 1993.
Meikle; The tissue, cellular, and molecular regulation of orthodontic tooth movement: 100 years after Carl Sandstedt; Eur J Orthod; 28(3):221-240; Jun. 2008.
Mermut et al.; Effects of interferon-gamma on bone remodeling during experimental tooth movement; Angle Orthod; 77(1):135-141; Jan. 2007.
Murphy: In Vivo Tissue Engineering for Orthodontists: A Modest First Step; Biological Mechanisms of Tooth Eruption, Resorption and Movement; Harvard Society for the Advancement of Orthodontics; pp. 385-410; Jan. 2006.
Piemonti et al.; Human pancreatic islets produce and secrete MCP-1/CCL2: relevance in human islet transplantion; Diabetes; 51(1):55-565; Jan. 2002.
Ren et al.; Cytokine profiles in crevicular fluid during orthodontic tooth movement of short and long durations; J Periodontol; 78(3):453-458; Mar. 2007.
Ren et al.; Cytokines in crevicular fluid and orthodontic tooth movement; Eur J Oral Sci; 116(2):89-97; Apr. 2008.
Rubin et al.; Inhibition of osteopenia by low magnitude, high-frequency mechanical stimuli; Drug Discov Today; 6(16):848-858; Aug. 16, 2001.
Rygh et al.; Activation of the vascular system: a main mediator of periodontal fiber remodeling in orthodontic tooth movement; Am J Orthod; 89(6):453-468; Jun. 1986.
Saito et al.; Interleukin 1 beta and prostaglandin E are involved in the response of periodontal cells to mechanical stress in vivo and in vitro; Am J Orthod Dentofacial Orthop; 99(3):226-240; Mar. 1991.
Sallusto et al.; Flexible programs of chemokine receptor expression on human polarized T helper 1 and 2 lymphocytes; J Exp Med; 187(6):875-883; Mar. 16, 1998.
Schneider et al.; Lymphotoxin and LIGHT signaling pathways and target genes; Immunol Rev; 202:49-66; Dec. 2004.
Seidenberg et al.; Is there an inhibitory effect of COX-2 inhibitors on bone healing?; Pharmacol Res; 50(2):151-156; Aug. 2004.
Shih et al.; Regional acceleration of remodeling during healing of bone defects in beagles of various ages; Bone; 6(5):377-379; Feb. 1985.
Shireman; The chemokine system in arteriogenesis and hind limb ischemia; J Vasc Surg; 45 Suppl A:A48-A56; Jun. 2007 (Author's Manuscript).
Teixeira et al.; Cytokine Expression and Accelerated Tooth Movement; J Dent Res; 89(10):1135-1141; Oct. 2010.
Tran Ma; Method for studying the vascular region of bone; J Pharmacol; 13:495-499; Jul.-Sep. 1982 (in French).
Uematsu et al.; Interleukin (IL)-1 beta, IL-6, tumor necrosis factor-alpha, epidermal growth factor, and beta 2-microglobulin levels are elevated in gingival crevicular fluid during human orthodontic tooth movement; J Dent Res; 75(1):562-567; Jan. 1996.
Verna et al.; Histomorphometric study of bone reactions during orthodontic tooth movement in rats; Bone; 24(4):371-379; Apr. 1999.
Viazis, A; Atlas of Orthodontics: Principles and Clinical Applications; WB Saunders Co.; pp. 205-213; Apr. 1993.
Vignery et al.; Dynamic histomorphometry of alveolar bone remodeling in the adult rat; Anat Rec; 196(2):191-200; Feb. 1980.
Way et al.; U.S. Pat. No. 15/329,586 entitled "Device and methods for osteoperforation," filed Jan. 27, 2017.
Wilcko et al.; Rapid Orthodontic Decrowding with Alveolar Augmentation: Case Report; World J Orthod; 4(3):197-205; Sep.-Nov. 2003.
Wilcko et al.; Rapid orthodontics with alveolar reshaping: two case reports of decrowding; Int J Periodontics Restorative Dent; 21(1):9-19; Feb. 2001.
Williams et al.; Orthodontic tooth movement analysed by the Finite Element Method; Biomaterials; 5(6):347-351; Nov. 1984.
Xu et al.; Interleukin-18 promoter gene polymorphisms in Chinese patients with systemic lupus erythematosus: association with CC genotype at position-607; Ann Acad Med Singapore; 36(2):91-95; Feb. 2007.
Yaffe et al.; Regional accelerated phenomenon in the mandible following mucoperiosteal flap surgery; J Periodontol; 65(1):79-83; Jan. 1994.
Yamamoto et al.; Cytokine production in human periodontal ligament cells stimulated with Porphyromonas gingivalis; J Periodontal s; 41(6):554-559; Dec. 2006.
Yao et al.; Osteoclast precursor interaction with bone matrix induces osteoclast formation directly by an interleukin-1-mediated autocrine mechanism; J Biol Chem; 283(15):9917-9924; Apr. 11, 2008.
Yen et al.; Closure of an unusually large palatal fistula in a cleft patient by bony transport and corticotomy-assisted expansion; J Oral Maxillofac Surg; 61(11):1346-1350; Nov. 2003.
Yoshimatsu et al.; Experimental model of tooth movement by orthodontic force in mice and its application to tumor necrosis factor receptor-deficient mice; J Bone Miner Metab; 24(1):20-27; Jan. 2006.
Zittermann et al.; Physiologic fluctuations of serum estradiol levels influence biochemical markers of bone resorption in young women; J Clin Endocrinal Metal; 85(1):95-101; Jan. 2000.
Examiner Requisition from the Canadian Patent Office for Canadian Application No. 2,835,838 dated Mar. 5, 2018, 3 pages.
Pandey, R.K. and Panda, S.S.; Drilling of Bone: A comprehensive review; J Clin Orthop Trauma; 4(1):15-30; Mar. 2013.
Lloyd, C.; Why You Should Drill Pilot Holes Before Screwing Into Wood; published online at https://www.howtogeek.com/298938/why-you-should-drill-pilot-holes-before-screwing-into-wood/; Mar. 2017.
Pal Singh, A; Bone Screws Used in Orthopedics; published online at https://boneandspine.com/bone-screws-used-in-orthopedics/.

* cited by examiner

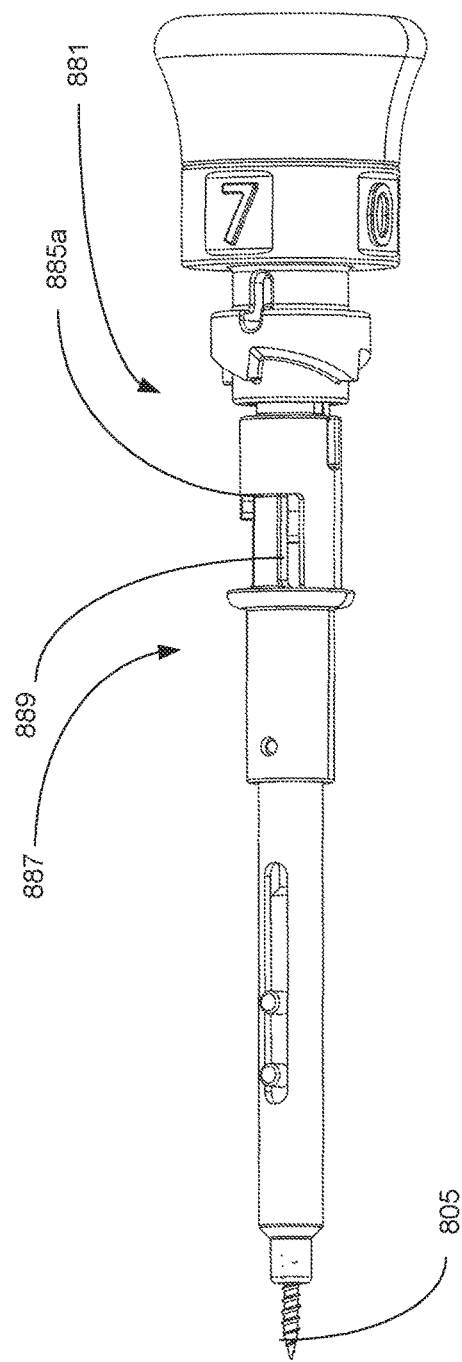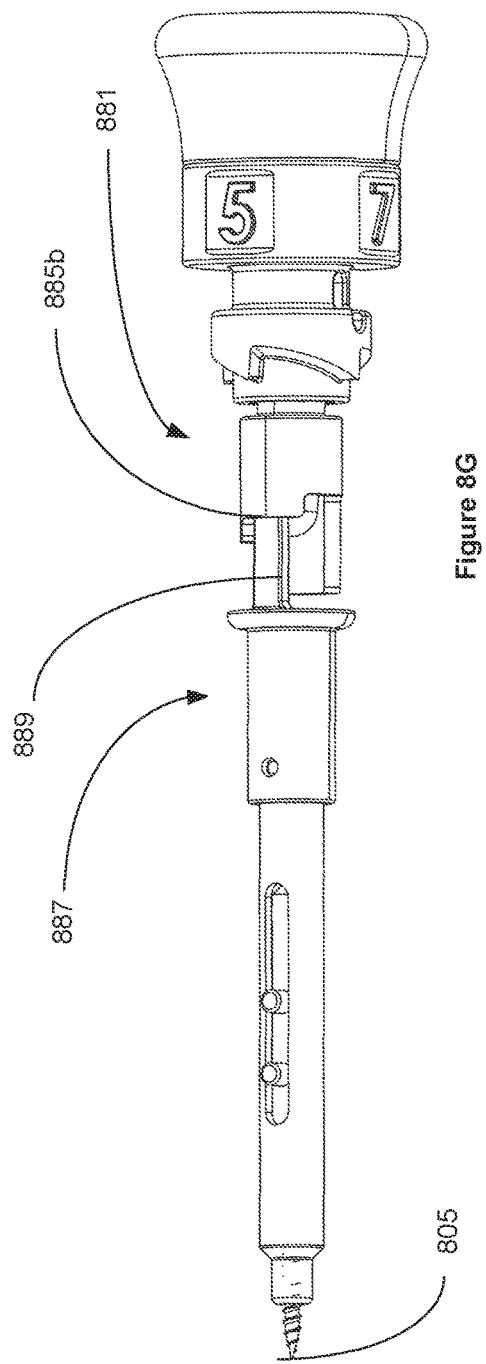

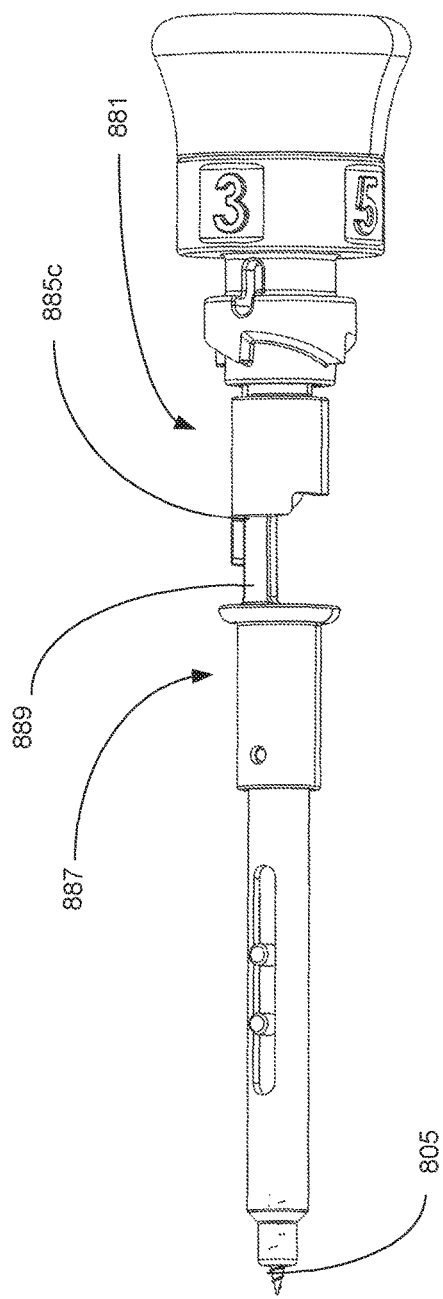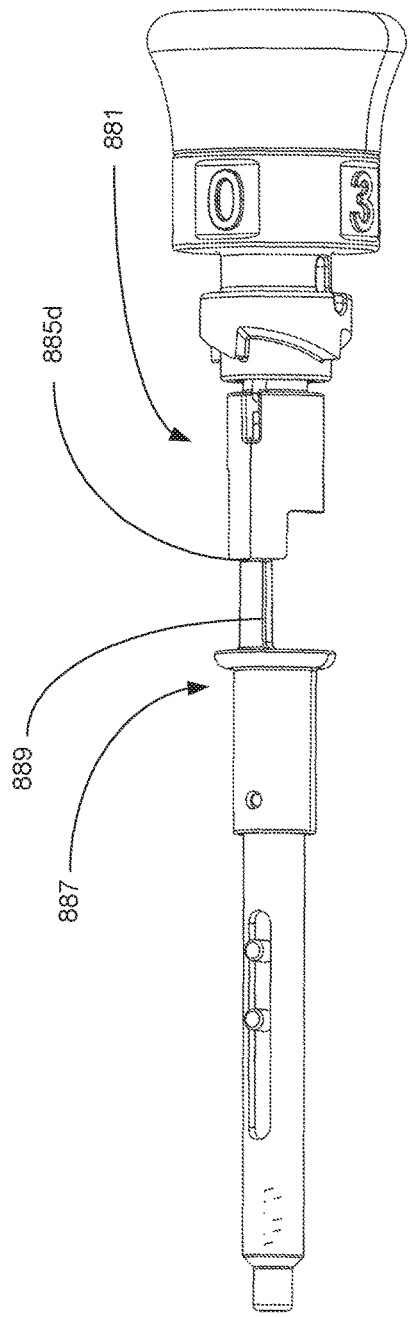
Figure 8H
Figure 8I

| | A | B | C | D | E |
|---|---|---|---|---|---|
| | | Diagnosis | Outcome | Est Regular Tx Time | Tx Time w/ PROPEL™ |
| | Case 1: 32 Year Old Woman | Large gap due to previous extraction of an unrestorable #30; Goal close the extraction space via protraction of #31 | All the extraction space was closed | 8 Months | 4 Months |
| | Case 2: 28 Year Old Man | Class II Div 1 left malocclusion; Goal: Obtain a Class I canine relationship on the left and reduce overjet via the unilateral extraction of #13. | All space closed and #12 had considerable mesial drift | 2 Months | 4 Weeks |
| | Case 3: 35 Year Old Woman | Congenitally missing lower 2nd premolars Mesial- Distal space was insufficient for implants | All the 2nd premolar spaces were closed | 6 Months | 3 Months |
| | Case 4: 12 Year Old Male | Tx of moderate upper and lower crowding with excessive overjet and overbite. | The space between #28 and #29 closed. | 12 Months | 5 Months |
| | Case 5: 24 Year Old Man | Severe shift of upper anterior teeth to the right (5-6mm) Lower arch needs minimal orthodontics treatment for correction of moderate crowding. | Complete canine retraction complete, followed by retraction of other anterior teeth | 24 Months | 11 Months |
| | Case 6:38 Year Old Woman | Excessive spacing Patient had been using an upper partial denture | Protraction of posterior teeth accomplished | 24 Months | 13 Months |
| | Case 7:45 Year Old Woman | Patient had very severe deep bite that was impinging on lower gingiva, very dense bone around upper anterior teeth and retroclined upper teeth | Overbite of patient was corrected and the remaining orthodontic treatment was accomplished | Traditional Ortho Ineffective | 11 Months |

FIG. 12

METHOD AND DEVICE FOR CAUSING TOOTH MOVEMENT

CROSS REFERENCE TO RELATED APPLICATIONS

This application is a continuation of U.S. patent application Ser. No. 15/208,401, filed Jul. 12, 2016, titled "METHOD AND DEVICE FOR CAUSING TOOTH MOVEMENT," which is a continuation of U.S. patent application Ser. No. 14/326,069, filed Jul. 8, 2014, titled "METHOD AND DEVICE FOR CAUSING TOOTH MOVEMENT," now U.S. Pat. No. 9,387,051, which is a continuation of U.S. patent application Ser. No. 14/073,778, filed Nov. 6, 2013, titled "METHOD AND DEVICE FOR CAUSING TOOTH MOVEMENT," now U.S. Pat. No. 8,770,969, which is a continuation of U.S. patent application Ser. No. 13/471,099, filed May 14, 2012, titled "METHOD AND DEVICE FOR CAUSING TOOTH MOVEMENT," now U.S. Pat. No. 8,602,777, which claims priority to U.S. Provisional Patent Application No. 61/486,038, filed May 13, 2011, and titled "METHOD AND DEVICE FOR CAUSING TOOTH MOVEMENT," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to dental and orthodontic devices and methods, particularly devices and methods for increasing the movement of teeth in the jaw.

BACKGROUND

A large percentage of today's children and adult population undergoes orthodontic treatments at some point in their lives to treat malocclusions (i.e. crooked teeth leading to poor bite) or improve skeletal abnormalities. Because growth and development of adult teeth is generally stagnant, treatment of malocclusions in adults requires reliance on the dento-alveolar element, e.g. the ability of teeth to move when a sufficient inflammatory response is created in the jaw.

The most common method of creating movement in teeth is through the use of braces. The braces include wires and other tensioning devices, such as rubber bands and coils or removable trays, that exert a continuous force on the tooth to move the tooth to a desired location. The use of braces to cause tooth movement, however, takes on average 18-24 months and can take up to 3-4 years, often causing both social and physical discomfort. Accordingly, it would be advantageous to have a treatment method that could successfully move a tooth or teeth in a shorter period of time.

SUMMARY OF THE DISCLOSURE

In general, in one aspect, a device for increasing movement of a tooth in a jaw includes a handle, an elongate member extending from the handle, a screw tip at a distal end of the elongate member, and a sleeve. The screw tip is configured to drill into the cortical bone of the jaw to increase movement of the tooth. The sleeve is configured to move along the elongate member to vary the length of exposed screw tip.

In general, in one aspect, a method of increasing movement of a tooth in a jaw includes moving a sleeve along an elongate member of a device to set a length of exposed screw tip; drilling a hole with the screw tip through a cortical bone of a jaw, wherein the jaw comprises at least one tooth having an orthodontic brace thereon; and stopping the drilling when the length of exposed screw tip has penetrated the jaw.

These and other embodiments can include one or more of the following features.

The sleeve can be configured to move along the elongate member to set the length of the exposed screw tip at between 0 mm and 10 mm. The sleeve can be configured to move along the elongate member in ½ mm increments.

The handle can further include a button configured to control movement of the sleeve. The handle can include a first end attached to the elongate member and a second end, and the first end can be rotatable with respect to the second end. The first end can be configured to control rotation of the screw.

A hole can be formed in a distal, mesial, facial or lingual surface of the jaw. There can be a plurality of holes formed along the mesial surface of the jaw. A hole can be formed into a gingival flap. A hole can be formed without cutting away gingival flap prior to forming the hole. The exposed screw tip can be approximately 3 mm, for example when the hole is drilled proximal to a central or lateral tooth or in the palatal. The exposed screw tip can be approximately 5 mm, for example when the hole is drilled proximal to a canine or a premolar. The exposed screw tip can be approximately 7 mm, for example when the hole is drilled proximal to a posterior molar or in the mandible. The sleeve can be configured to act as a drill stop.

The device can further include a pressure transducer at the distal end of the sleeve. There can be a pressure indicator on the handle, and the pressure indicator can be configured to indicate the pressure measured by the pressure transducer.

The handle can include a plunger and a torque translator, and axial movement of the plunger can cause rotation of the screw tip.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A-8I show an embodiment of a dental device having a ratchet knob to set the screw tip and predetermined lengths.

FIG. 12 is a chart summarizing results obtained during studies of the use of the dental device described herein.

DETAILED DESCRIPTION

Figure 1A:
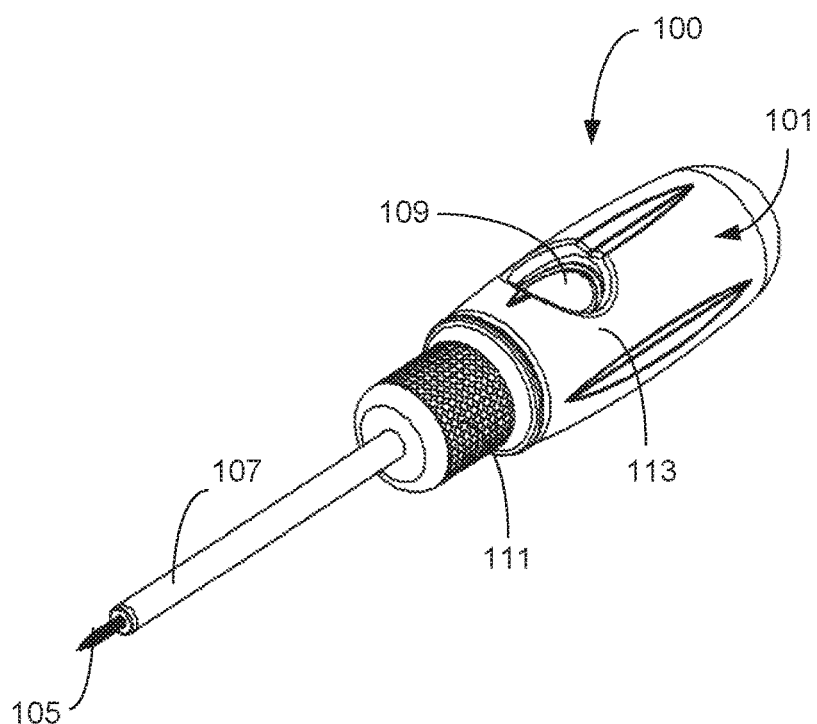
FIG. 1A shows an embodiment of a dental device having an exposed screw tip.
Figure 1B:
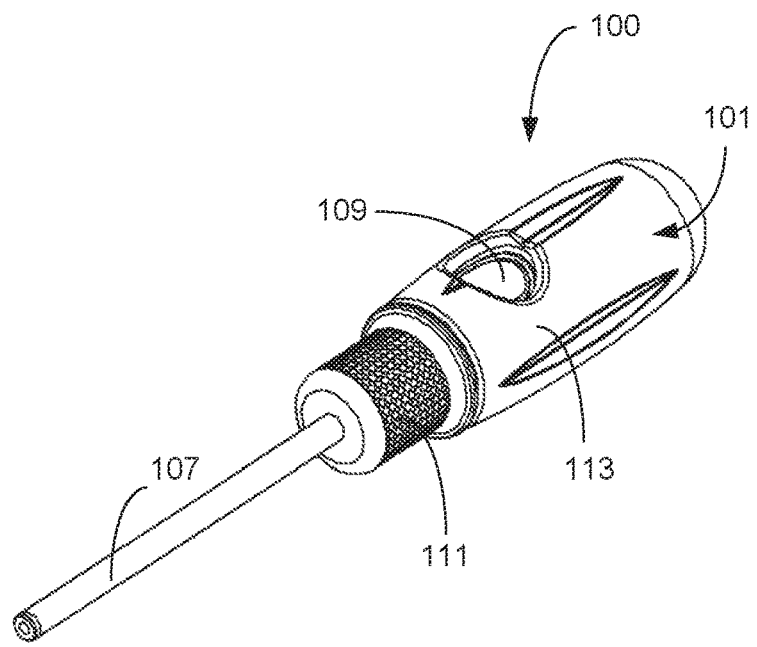
FIG. 1B shows the dental device of FIG. 1A having a covered screw tip.
Figure 2:
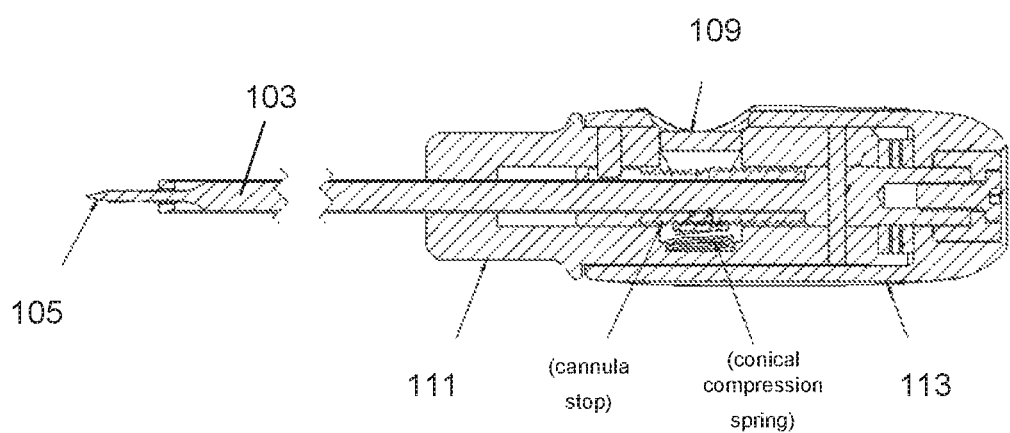
FIG. 2 is a cross-section of the dental device of FIG. 1A.
Figure 3A:
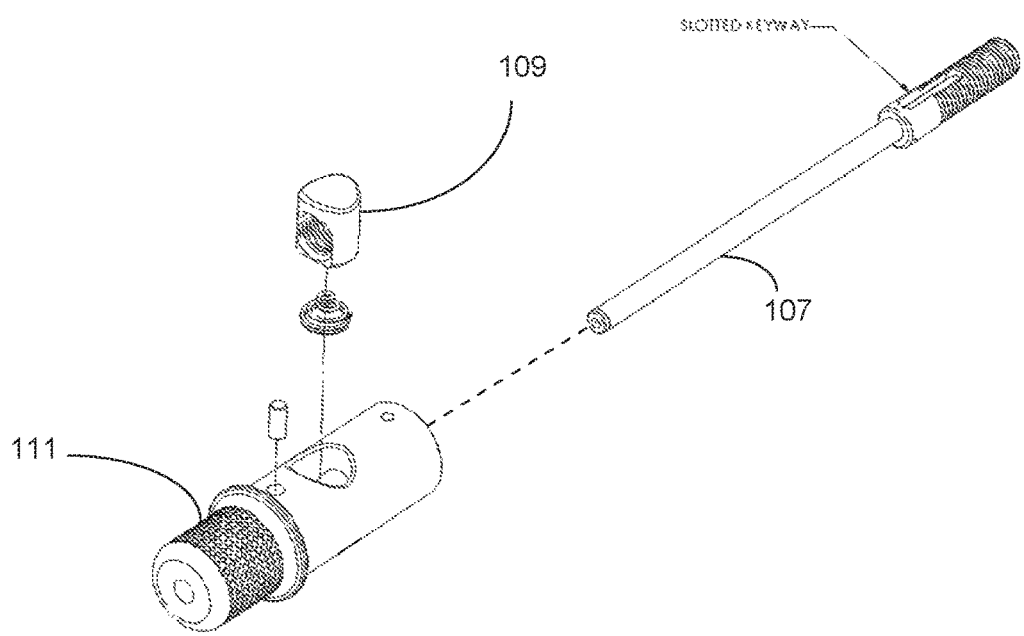
FIGS. 3A-3C are exploded views of the device of FIG. 1A.
Figure 3B:
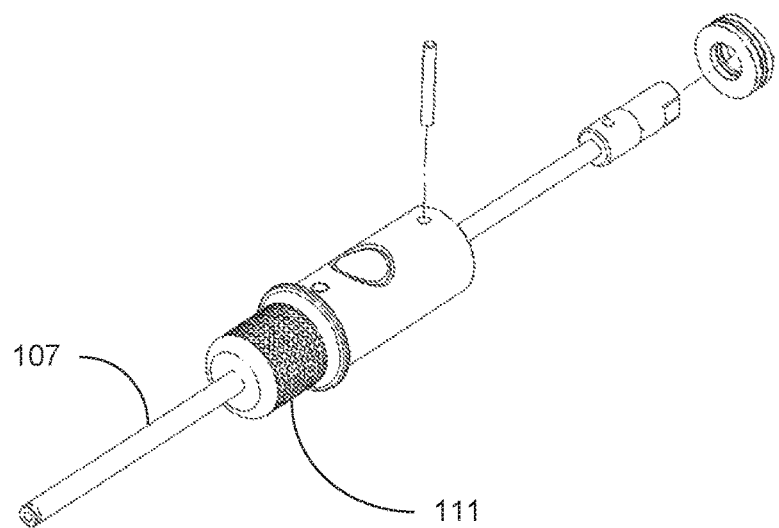
Figure 3C:
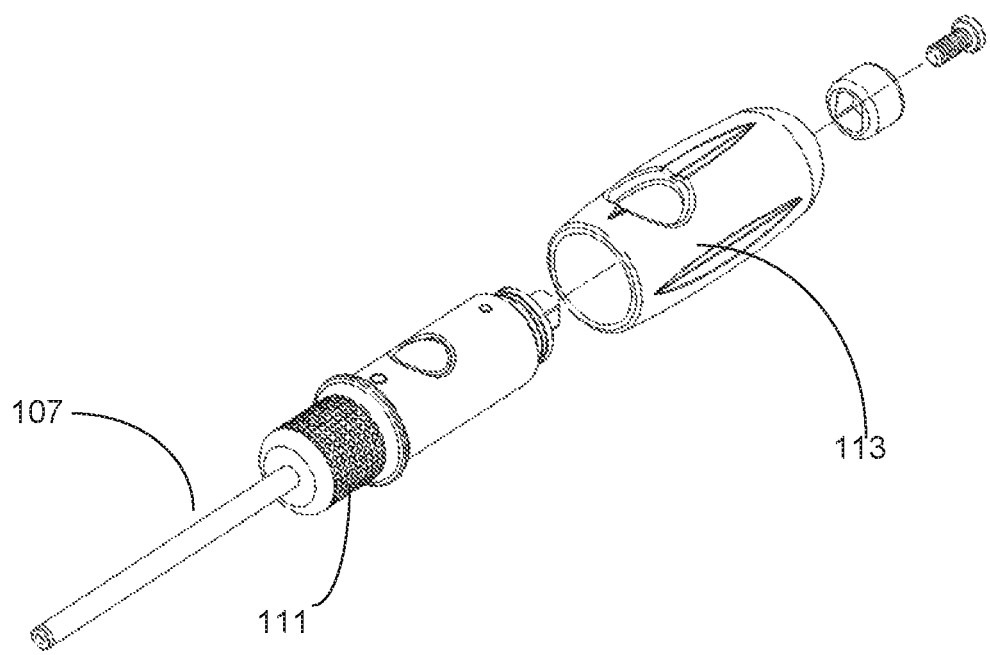
Figure 4:
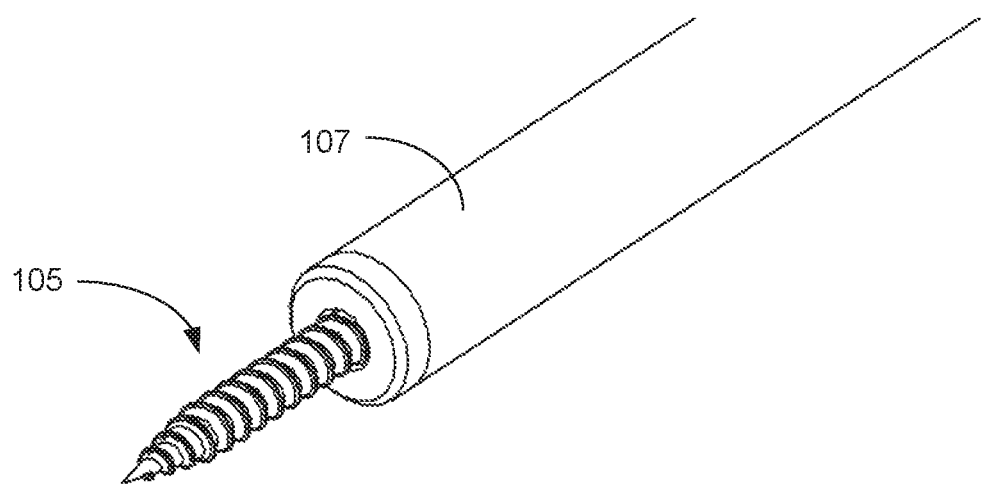
FIG. 4 shows a close-up of the screw tip of the device of FIG. 1A.

Referring to FIGS. 1-4, a device 100 is a hand-held instrument to create micro-osteoperforation in bone and soft tissue, i.e. the device 100 can be used to increase the movement of a tooth in a jaw. The device 100 includes a handle 101 and an elongate shaft 103 extending from the handle 101. A screw tip 105, for example made of stainless steel, can be located at the distal end of the elongate shaft 103. A sleeve 107 can be configured to move along the elongate shaft 103 to vary the length of exposed screw tip 105 (the screw tip 105 is shown exposed in FIG. 1A and fully covered in FIG. 1B).

The sleeve 107 can be released by a release mechanism, such as a button 109 on the handle 101. When compressed, the button 109 can allow the sleeve 107 to move along the shaft 103, and when released, the button 109 can lock the sleeve 107 in place. The button 109 can thus allow the screw tip 105 to be set at a desired length, for example at a length of between 0 mm and 10 mm. Further, in some embodiments, the device 100 can be configured to lock the length at specific increments, for example ½ mm increments. The sleeve 107, by covering all of the screw tip except the exposed portion, can act as a perforation tip depth stop to prevent the screw tip 105 from penetrating the bone beyond the targeted depth.

The shaft 103 and screw tip 105 can be rotatable with respect to the handle 101 or a portion of the handle 101. For example, the handle 101 can include a first end 111 attachable to the shaft 103 and a second end 113 configured to be held stationary by the user. The first end 111 can be rotatable with respect to the second end 113 so as to control rotation of the shaft 103, and hence rotation of the screw tip 105.

Figure 5A:
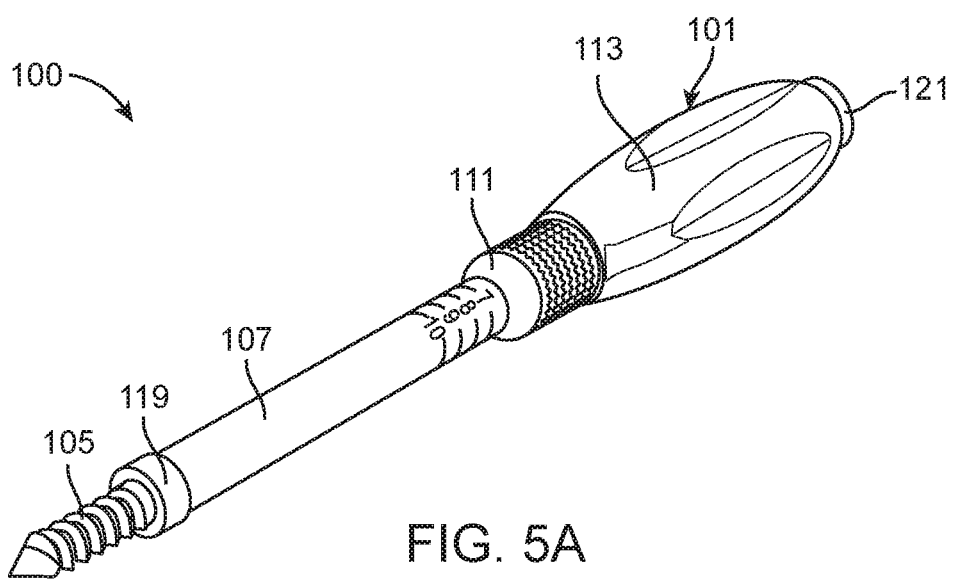
FIGS. 5A-5B show an embodiment of a dental device having a pressure transducer to determine when the screw trip has reached a particular depth.
Figure 5B:
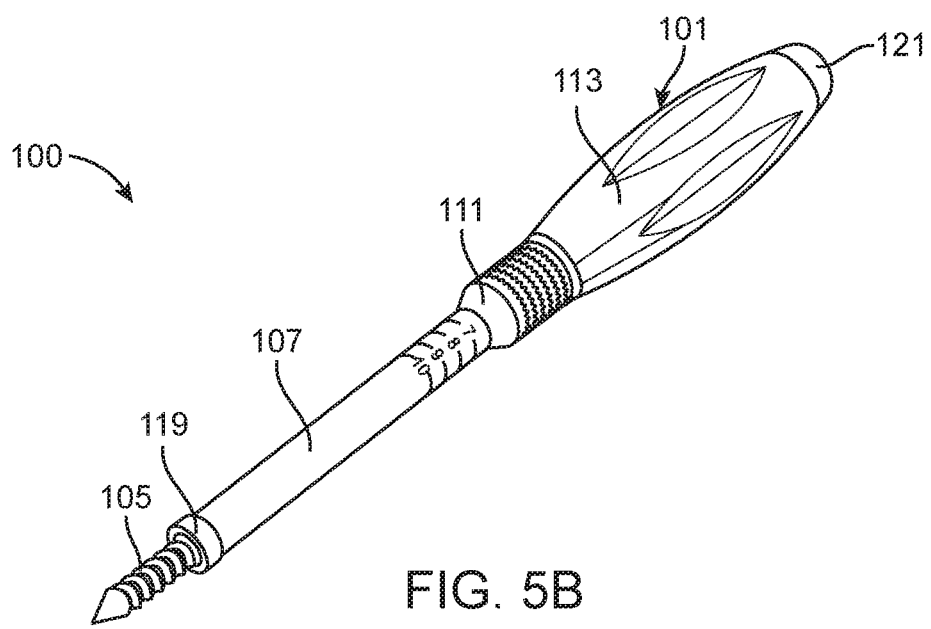

Referring to FIGS. 5A and 5B, in some embodiments, the dental device 100 can further include a pressure transducer 119 on the distal end of the sleeve 107 to determine when the screw tip 105 has fully penetrated the jaw or reached the predetermined depth. An indicator mechanism, such as an indicator light 121 on the handle 101, can be used to indicate that the screw tip 105 has penetrated the jaw fully. For example, the indicator light 121 can change colors from a dark color (see FIG. 5A), such as green, to a light color (see FIG. 5B), such as yellow, to indicate that the pressure transducer 112 has reached the patient's gums or when the pressure transducer 119 has measured a preset pressure.

Figure 6A:
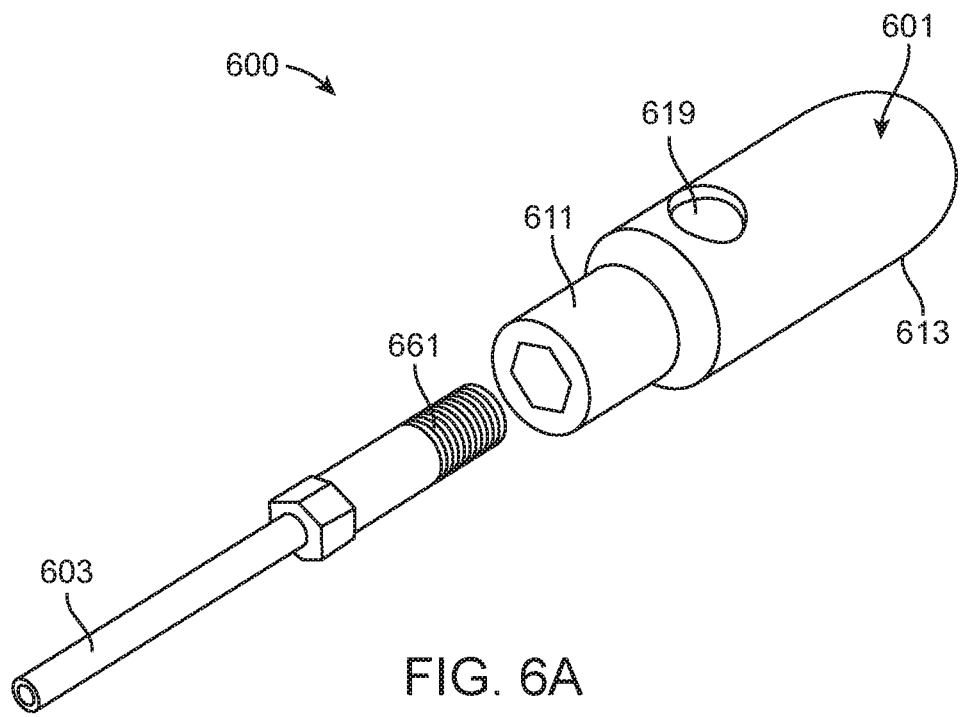
FIGS. 6A-6B show an embodiment of a dental device having a separable handle and shaft.
Figure 6B:
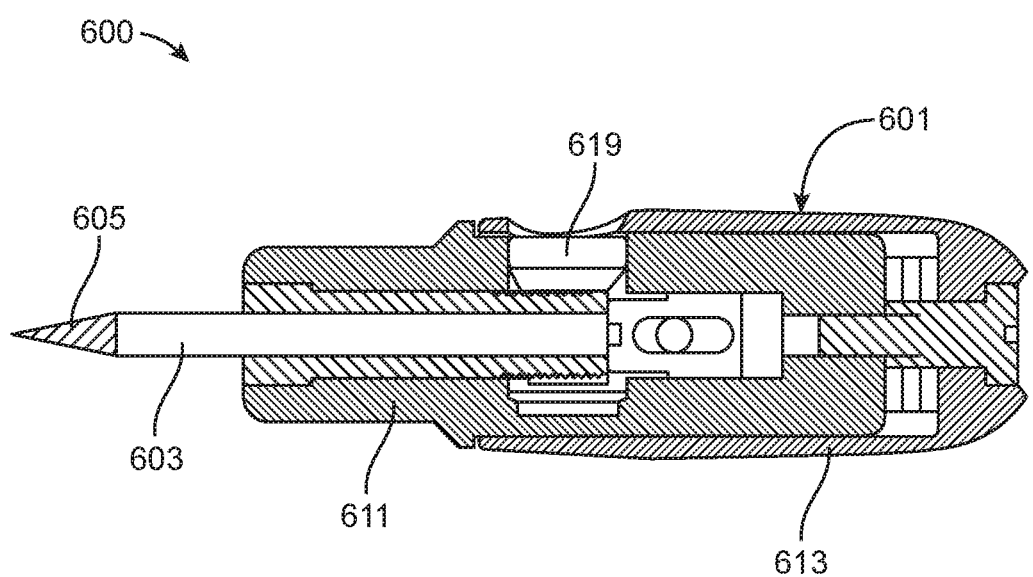

In some embodiments, referring to FIGS. 6A-6B, a dental device 600 can include a shaft 603 that is separable from the handle 601. The shaft 603 can include a screw tip 605 attached thereto. In some embodiments, the screw tip 605 can be always exposed, i.e., not be coverable by a sleeve and/or have variable length settings. The screw tip can have a length between 0 and 6 mm. Similar to the dental device 100, the shaft 603 and screw tip 605 can be rotatable with respect to the handle 601 or a portion of the handle 601. For example, the handle 601 can include a first end 611 attachable to the shaft 603 and a second end 613 configured to be held stationary by the user. The first end 611 can be rotatable with respect to the second end 613 so as to control rotation of the shaft 603, and hence rotation of the screw tip 605. The shaft 603 can include an attachment portion 661 that is configured to snap or screw into the handle 601. For example, as shown in FIGS. 6A and 6B, the attachment portion can include teeth configured to interlock with teeth inside the handle 601. Further, the shaft 603 can snap in and out of the handle 601 through a release mechanism, such as a button 619. In some embodiments, a spring can be included proximal to the release mechanism to urge the shaft 603 out of the handle 601 when the release mechanism is activated. Advantageously, by having the shaft 603 be removable from the handle 601, the handle 601 can be used with different shafts 603, thereby allowing the shafts 603 to be disposable and the handle 601 to be reusable.

Figure 7:
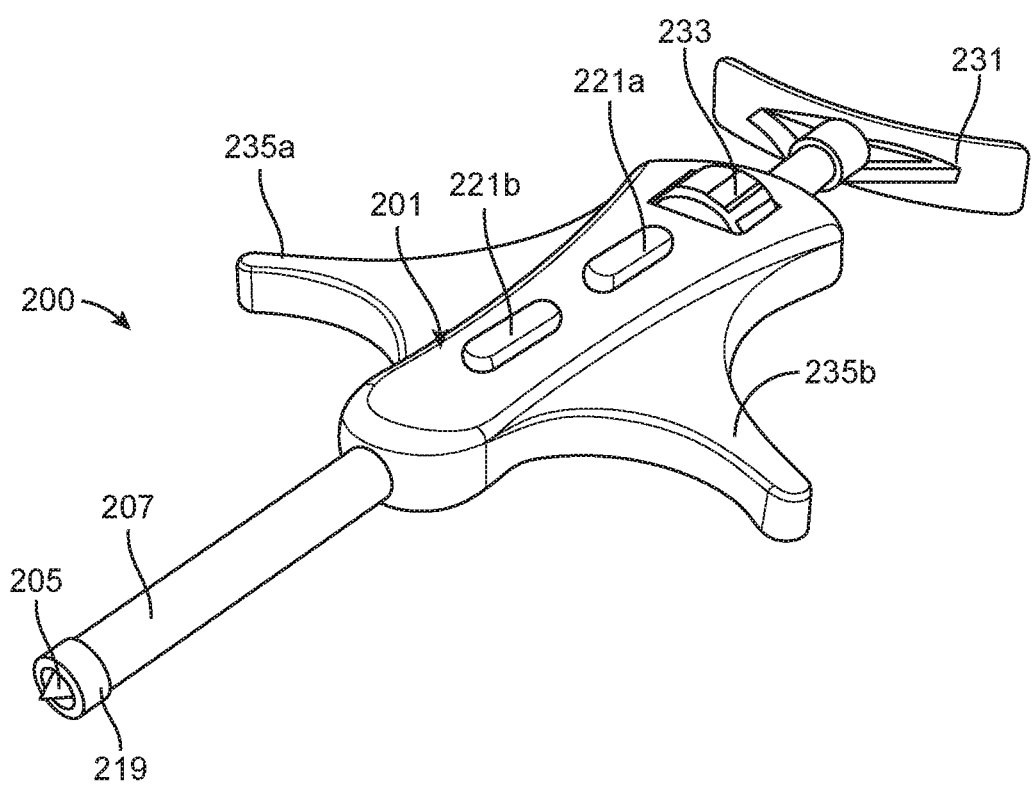
FIG. 7 shows an embodiment of a dental device having a plunger and torque translator to cause rotation of the screw tip.

Referring to FIG. 7, a dental device 200 can include many of the same elements as the dental device 100, such as the screw tip 205, sleeve 207, and handle 201. The handle 201 can include a plunger 231 and a torque translator 233 such that axial movement of the plunger 231 causes rotation of the screw tip 205. Further, the handle 201 can include wings 235a, 235b to allow for better gripping of the handle. Similar to the embodiment of FIG. 5, the dental device 200 can include a pressure transducer 219 to determine when the screw tip 205 has reached the patient's gums. In contrast to the single indicator of FIG. 5, the device 200 can include multiple indicators. For example, there can be two indicator lights 221a, 221b to indicate when the pressure transducer 219 has reached the gums, i.e. has sensed a preset pressure. For example, indicator light 221a can be a green light that indicates that the screw tip 205 can be advanced further, while indicator light 221b can be a red light indicating that the screw tip 205 should not be advanced further.

Referring to FIGS. 8A-8E, a dental device 800 can include a handle 801 and a shaft 803 having a screw tip 805 attached thereto. Similar to other embodiments described herein, the shaft 803 and screw tip 805 can be rotatable with respect to the handle 801 or a portion of the handle 801. For example, the handle 801 can include a first end 811 attachable to the shaft 803, such as via pins 875 (see FIG. 8D). Further, the second end 813 configured to be held stationary by the user. The first end 811 can be rotatable with respect to the second end 813 so as to control rotation of the shaft 803, and hence rotation of the screw tip 805. In the embodiment of FIGS. 8A-8E, almost the entire device can be rotatable except for a small second end 813. As a result, the second end 813 can be used to place distally-directed pressure on the device 800 to help puncture the tissue while the rest of the device can rotate to assist in screwing the screw tip 805 into the tissue.

Figure 8A:
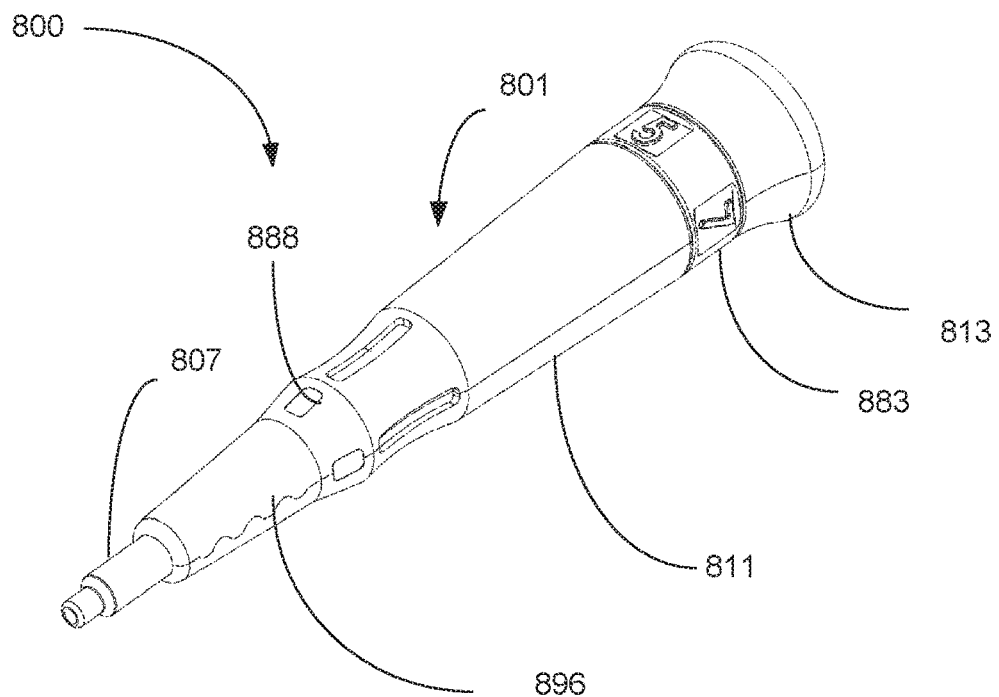
Figure 8B:
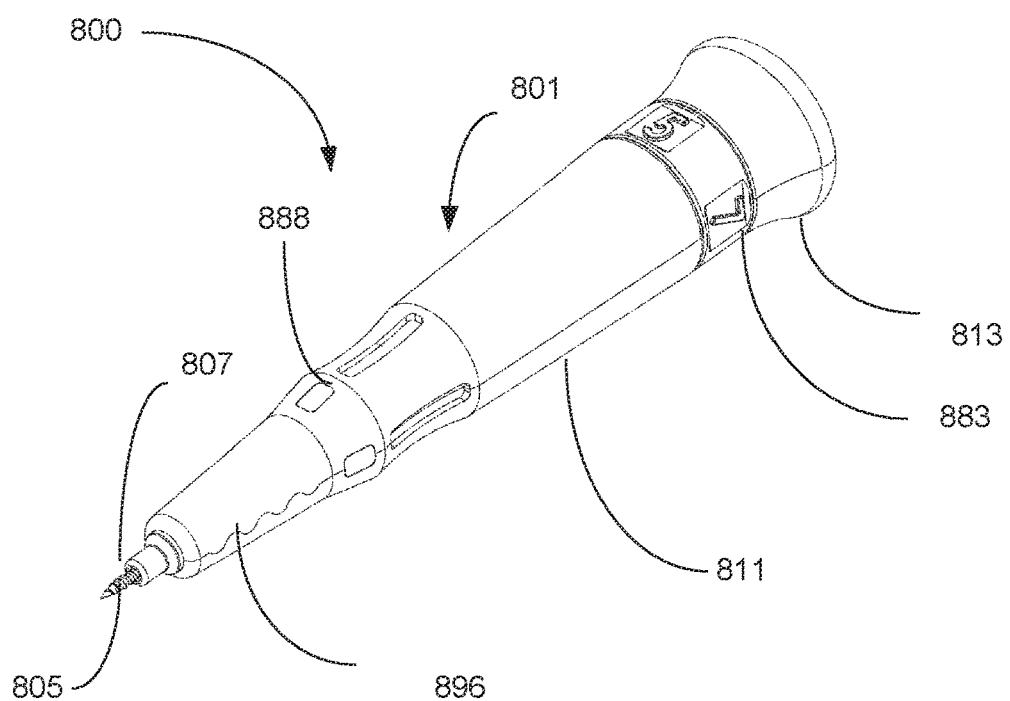

A sleeve 807 can be configured to move within the handle 801 and axially along the shaft 803 to vary the length of the exposed screw tip 805 (the screw tip 805 is shown exposed in FIG. 8B and fully covered in FIG. 8A). A ratcheting mechanism 881 can be used to set the sleeve 807 at the desired length. For example, the ratcheting mechanism 881 (see FIGS. 8C-8E) can be set such that the screw tip 805 is exposed at 2 mm increments, such as at 0 mm, 3 mm, 5 mm, and 7 mm. The ratcheting mechanism 881 can include a rotatable ratchet nob 883 that can be used to set the sleeve 807 such that the screw tip 805 is exposed at the desired length. The ratchet nob 883 can be attached to a plurality of ratchet stops 885 having different axial lengths. The ratchet nob 883 and ratchet stops 885 can be rotatable within the handle 801 with respect to a locking portion 887. The locking portion 887 can include a lock stop 889 configured to engage with one of the ratchet stops 885 to set the exposed length of the screw tip 805. Further, a spring 891 can bias the shaft 803 and screw tip 805 distally. Thus, as shown in FIG. 8D, the sleeve 807 will continue to cover the screw tip 805 until a proximal force is placed on the sleeve 807, such as by tissue. Referring to FIG. 8E, once the proximally directed force is placed on the sleeve 807, the sleeve 807 will move proximally against the spring 891 until the lock stop 889 engages with the set ratchet stop 885. If a different length of exposed screw tip 805 is desired, the ratchet nob 883 can be rotated, thereby rotating the ratchet stops 885 such that the lock stop 889 is forced to engage with a ratchet stop 885 that is of a different axial length.

The position of the ratchet stops 885 relative to the lock stop 889 for an exemplary device with four settings of 0 mm, 3 mm, 5 mm, and 7 mm, are shown in FIGS. 8F-8I. For example, in FIG. 8F, the lock stop 889 is in contact with a ratchet stop 885a at the 7 mm position, thereby exposing 7 mm of the screw tip 805. In FIG. 8G, the lock stop 889 is in contact with a ratchet stop 885b at the 5 mm position, thereby exposing 5 mm of the screw tip 805. In FIG. 8H, the lock stop 889 is in contact with a ratchet stop 885c at a 3 mm position, thereby exposing 3 mm of the screw tip 805. Finally, in FIG. 8I, the lock stop 889 is in contact with a ratchet stop 885d at a 0 mm position, thereby keeping the screw tip 805 fully exposed.

Referring to FIGS. 8A-8E, the distal end 880 of the sleeve 807 can be configured to sit against the outer portion of the gums after the screw tip 805 has fully penetrated the gums. Further, a pressure transducer, such as an LED indicator 888, can be used in the device 800 to indicate when the screw tip 805 has reached the desired depth in the tissue. The LED indicator 888 can work, for example, by including a battery 893 with a flexible negative lead 895 in contact with the battery 893 and a positive lead 897 spaced away from the battery 893, such as with a compression spring 899. Both leads 895, 897 can be connected to an LED light 898. As the sleeve 807 makes contact with the ratchet stops 885, the positive lead 897 can be pushed against the battery 893. When contact is made, the LED light 898 can turn on, which can shine light through the LED indicator 888, indicating that the desired screw length, and thus the desired microperforation depth, has been achieved.

Figure 8C:
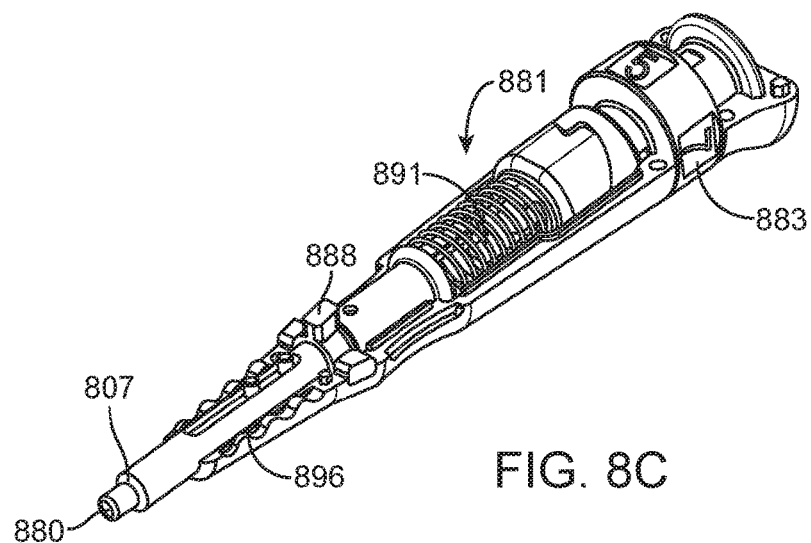
Figure 8D:
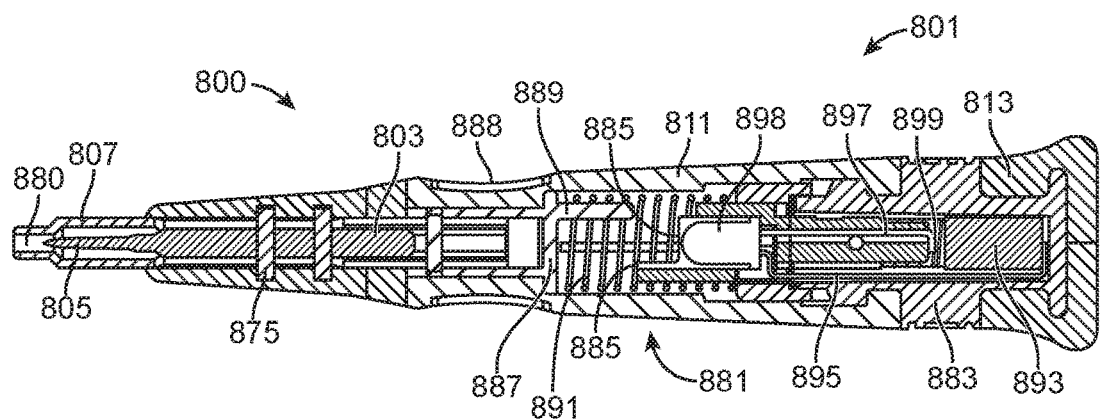
Figure 8E:
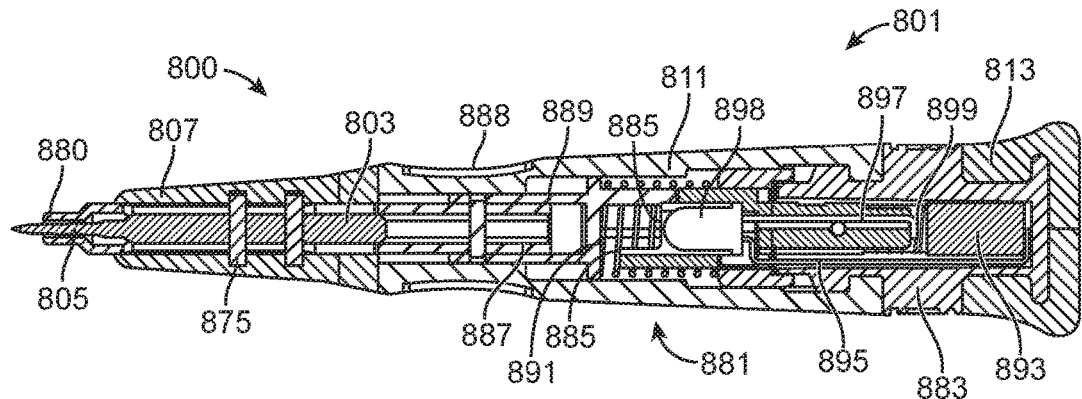

Referring to FIGS. 8A-8C, the handle 801 can be made of two or more pieces of material connected together. In order to prevent torque, i.e., torque caused during rotation of the screw tip 805 to cause microperforation, at least some of the joints can include undulations 896 at the seams.

Referring to FIGS. 9A-9E, in one embodiment, a dental device 700 can include a handle 701 and a shaft 703 having a screw tip 705 attached thereto. The device 700 can include any of the features of the devices described above, e.g., can include a rotatable portion and a stationary portion, a sleeve configured to expose the screw tip, etc. The device 700 can be configured to deliver a fluid, such as anesthesia, near or into the tissue during use. A fluid cartridge 770 can be located inside the handle 701 and be configured to hold delivery fluid therein. Further, the screw tip 705 can include holes 771 (see FIG. 9E) extending therethrough, for example, the screw tip 705 can be porous, to allow the fluid to pass therethrough. In one embodiment, the screw tip 705 can be formed of stainless steel, for example 17-4 stainless steel, and can be annealed and heat treated to form the holes 771. The holes 771 can be configured to allow a fluid, such as anesthesia, to pass through the screw tip 705. A hypodermic needle 773 can be connected to the shaft 703, which can puncture the fluid cartridge 770 when pressure is applied thereto by a plunger 775. Accordingly, fluid from the cartridge 770 can travel through the fluid path in the shaft 703 and screw tip 705 and out through the holes 771 to be delivered to the patient.

Figure 9A:
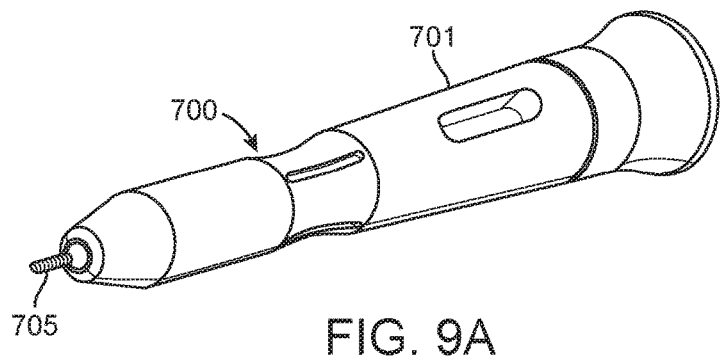
FIGS. 9A-9E shows an embodiment of a dental device having a screw tip with holes therein for fluid delivery.
Figure 9B:
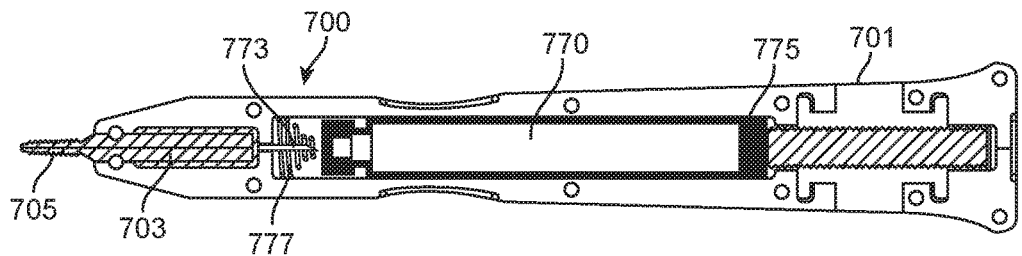
Figure 9C:
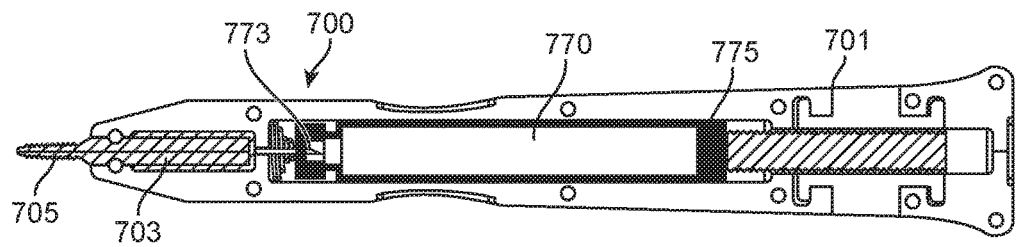
Figure 9D:
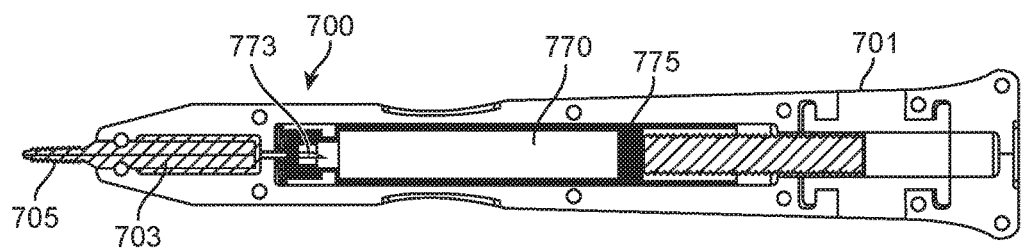
Figure 9E:
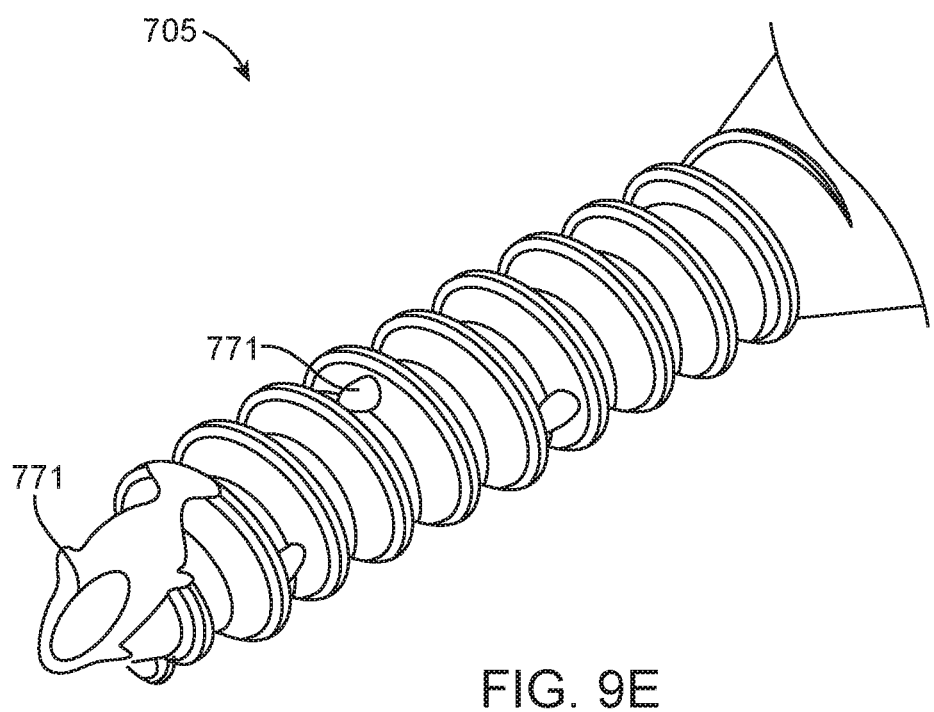

The plunger 775 of the device 700 can be a threaded plunger that shuttles axially, such as by rotating a knob. As shown in FIGS. 9A and 9B, when moved distally, the plunger 775 can be configured to push the cartridge 770 toward the hypodermic needle 773 to puncture the cartridge 770. As shown in FIGS. 9A and 9B, after the hypodermic needle 773 has punctured the cartridge 770, the plunger 775 can be configured to dispense fluid as the plunger is moved further distally. A compression spring 777 can prevent the cartridge 770 from being accidentally punctured by the hypodermic needle 773 when the plunger is in the retracted position. The screw tip 705 and/or fluid delivery aspects of the dental device 700 can be used with any of the devices 100, 200, 300 described herein.

Figure 10A:
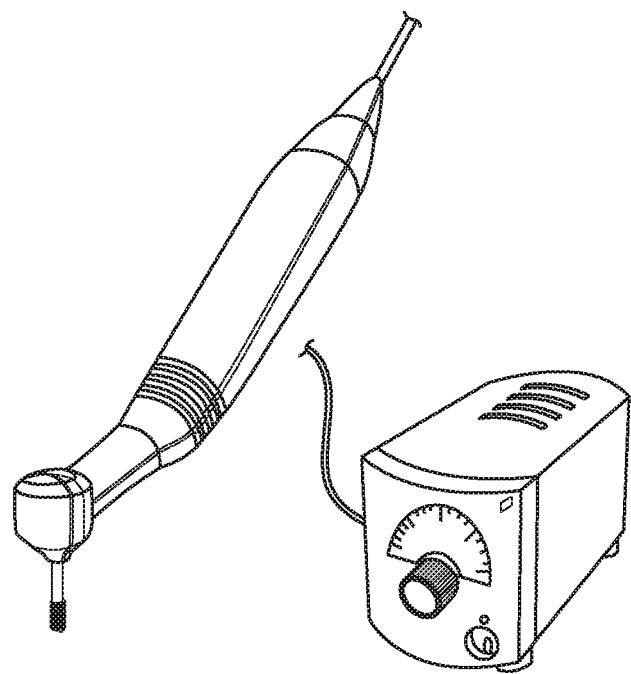
FIG. 10A shows a microperforation dental device having a mechanically powered distal tip.
Figure 10B:
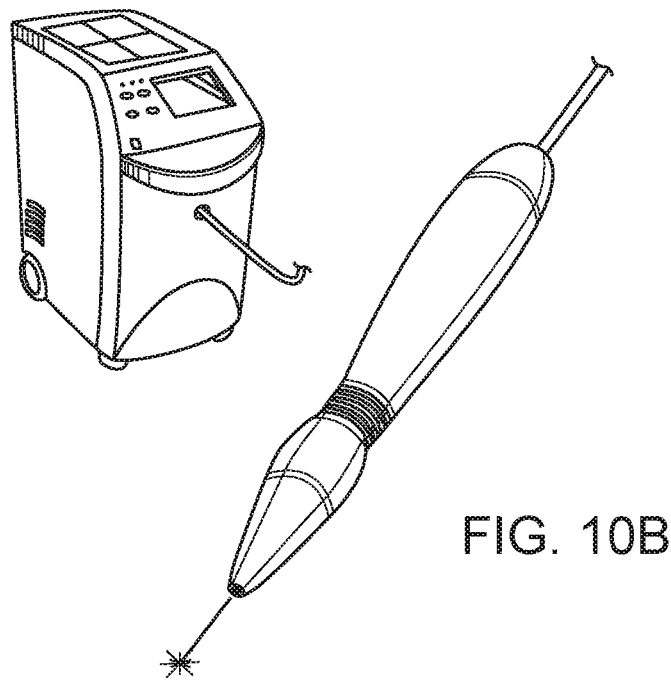
FIG. 10B shows a microperforation dental device having a laser on the distal end.
Figure 10C:
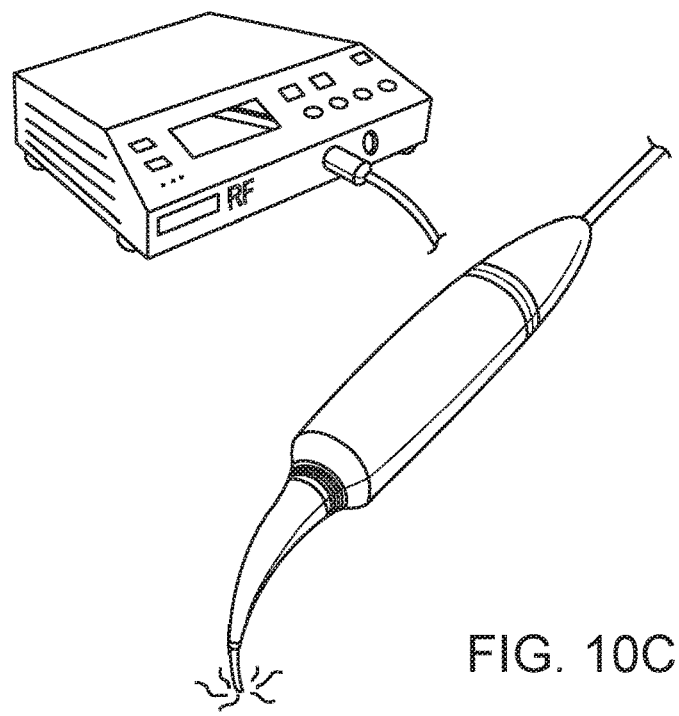
FIG. 10C shows a microperforation dental device having a radiofrequency source on the distal end.
Figure 10D:
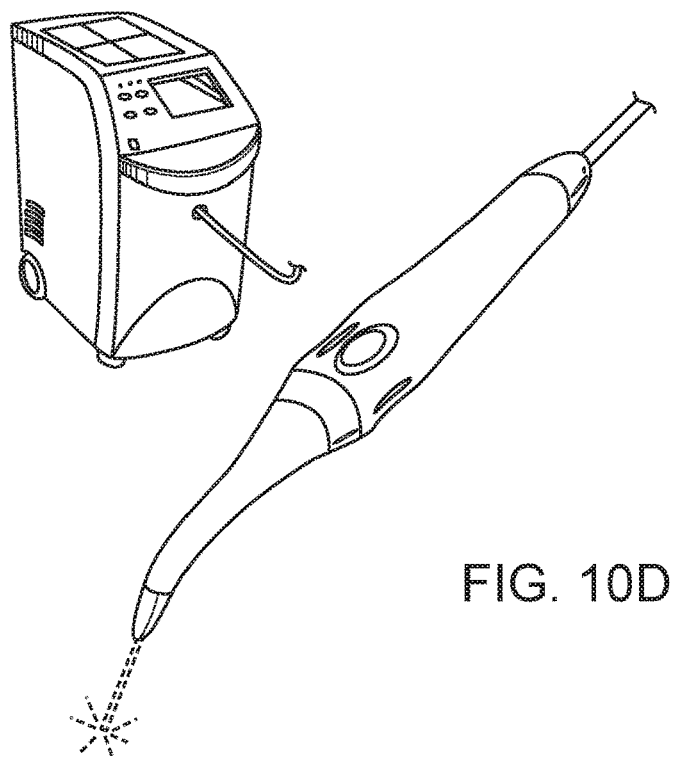
FIG. 10D shows a microperforation dental device having a water jet on the distal end.

In some embodiments, the devices described herein can be single use devices. Further, in some embodiments, the devices described herein can be operated using manual power. In other embodiments, the devices described herein can be operated electric power. Further, in some embodiments, different energy sources can be used in place of the screw tip. For example, the device can be powered with a power source (see FIG. 10A), such as to rotate a distal screw or apply vibratory forces, can include a laser in the distal end (see FIG. 10B), can include a radiofrequency source on the distal end (see FIG. 10C), or a water jet on the distal end (see FIG. 10D). One or more of these energy sources can be used in place of or in addition to the screw tip of the devices described herein.

Figure 11A:
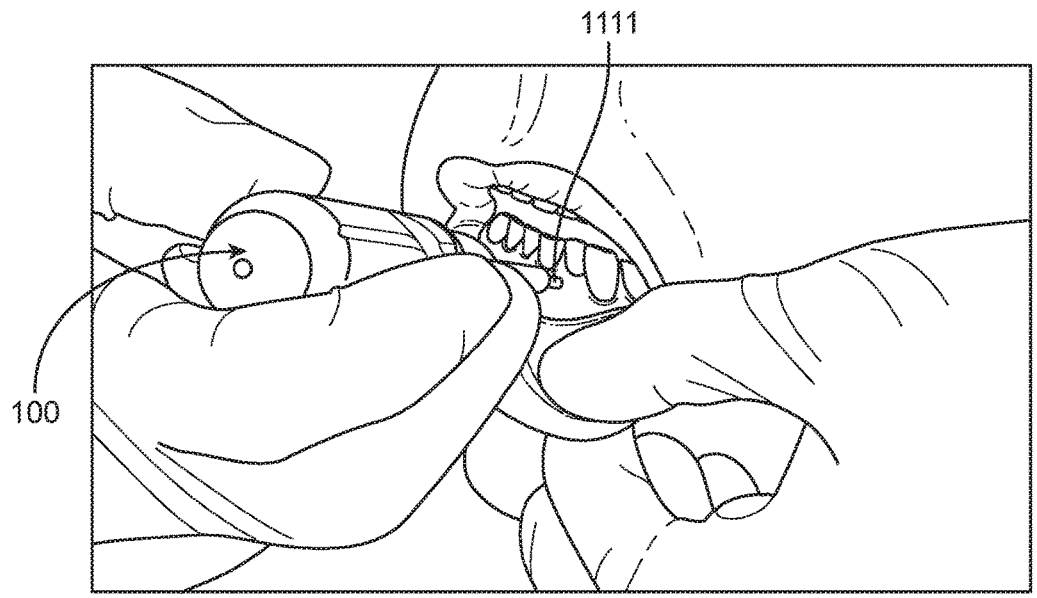
FIGS. 11A and 11B show use of a dental device to create microperforations.

In use, any of the devices 100, 200, 300, 600, 800, 900 described herein can be used to enhance the movement of a tooth or teeth in a jaw. For example, referring to FIGS. 11A and 11B, the device 100 can be used to form perforations or holes 1111 in the jaw 1113 of a patient, called "osteoperforation." To do so, the button 109 can be depressed while pulling the sleeve 107 toward the handle 101 to extend the screw tip 105. The sleeve 107 can be adjusted to obtain the desired length of screw tip 105. The button 109 can then be released, locking the screw tip 105 at the desired length. The device 100 can be held at approximately a 90 degree angle to the patient's gingival while keeping the tissue taunt. The screw tip 105 can be rotated against the gums by rotating the handle 101, for example in a clockwise direction. Pressure can be applied to the device 100, which, in combination with the rotation of the screw tip 105, can cause a cutting edge of the screw tip to form one or more holes, such as between 1 and 10 holes, for example approximately 3 holes, in the gingival flap of the jaw 113, for example through a mesial surface of the jaw and/or through cortical bone of the jaw. Each hole in the jaw can be formed without cutting away a gingival flap prior to formation of the hole. Further, each hole can be formed in the cortical bone near a malocclusion sought to be treated. The pressure and rotation can be stopped when the desired depth has been reached, i.e. when the screw tip 105 has been advanced all the way into the jaw and further penetration has been stopped by the sleeve 107. Holes of between 0 mm and 10 mm deep can be formed, such as holes of approximately 3 mm, 5 mm, or 7 mm. The handle 101 can be rotated in the opposite direction, for example counter-clockwise, to remove the device from the jaw. In is to be understood that the other devices described herein can work in a similar fashion.

Figure 11B:
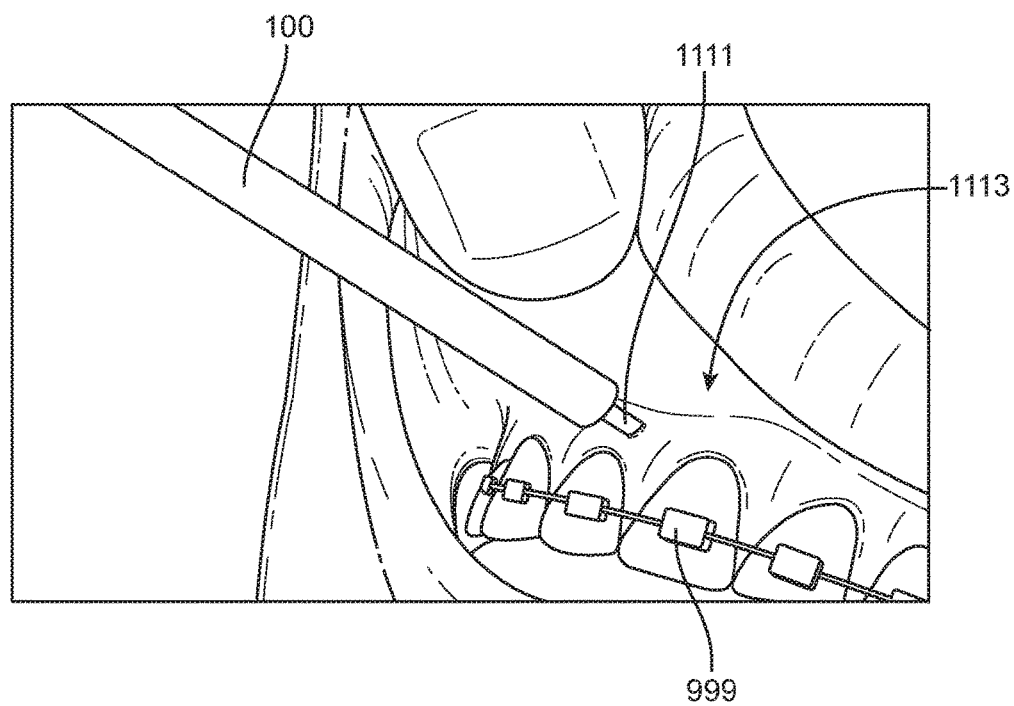

Referring to FIG. 11B, in some embodiments, the devices described herein, such as device 100, can be used in conjunction with braces 999 or other orthodontic devices.

The holes 1111 formed in the jaw 1113 can create an inflammatory response within the jaw. As a result, osteoclast precursors and cytokines can be drawn to the site of the holes 1111. The cytokines can promote osteoclast formation and activation, causing increased bone remodeling and movement. The holes 1111 formed in the jaw 1113 can thus allow a tooth or teeth to move over time to partially or fully treat the malocclusion.

The devices described herein can be used to correct major molar uprighting, major lower molar protraction, major canine protraction, and major intrusion. Referring to FIG. 12, the devices described herein can be used to treat a variety of conditions, such as reducing large gaps between teeth caused by extractions, increasing the gap between teeth to make space for implants, reducing overjet and overbite, and reducing overcrowding (see column B). The time required for treatment of such conditions using the devices described herein (see column E) can be significantly reduced relative to the established traditional time for treatment with braces (see column D). When ostoperforation is used with the devices described herein, the treatment time for such malocclusions can be decreased by over 30%, such as over 40%, for example by more than 50%, relative to the use of braces. For example, the time for treatment can be reduced from 8 months to 4 months, 2 months to 4 weeks, 6 months to 3 months, 12 months to 5 months, 24 months to 11 months, 24 months to 13 months (see columns D and E).

Advantageously, all of the devices described herein can be configured to have an adjustable-length screw tip. The adjustable length allows the devices to be controlled more precisely during the formation of holes and therefore allows the devices to be accurately and safely used in bone of different thicknesses and/or densities. Accurate and safe use of the device in bone of different thicknesses and/or densities allows the device to be used in different patients and in different types of teeth. For example, the maxilla is thinner than the mandible and therefore requires the formation of holes of a smaller depth than holes formed in the mandible. Likewise, the depth of penetration required to perforate through cortical bone into cancellous bone increases when moving from the maxilla or mandible posteriorly. As another example, an athletic male patient will typically have thicker and/or denser teeth than a young female or an elderly woman. Accurately and safely setting the screw tip length, and thus the depth of penetration, can allow the device to be used in any of these scenarios. Further, the same device could advantageously be used to drill holes of different depths near two different teeth of the same patient.

In one aspect, the screw tip can be set to approximately 3 mm when forming holes proximal to a central or lateral tooth or in the palatal. In another aspect, the screw tip can be set to approximately 5 mm when forming holes proximal to a canine, a premolar, or a molar in a female or a small male. In another aspect, the screw tip can be set to approximately 7 mm when forming holes proximal to posterior molars, in the mandibular, or in the maxillary in large men.

Use of the device described herein for osteoperforation advantageously taps a bone metabolism process that safely accelerates motion. The microperforation process using the devices described herein is safe, simple, and produces local alveolar bone reactions that enable rapid motion of teeth. Further, the process can be performed in-office and, as described above, can be performed precisely for a broad range of patients and in a broad range of different types of teeth.

What is claimed is:

1. A method of increasing movement of a tooth in a jaw by provoking an inflammatory response, the method comprising:
   (a) holding a handle of a device, the device having an elongate member extending from the handle and a screw tip at a distal end of the elongate member;
   (b) contacting the screw tip of the device with gingival tissue at a predetermined site on the gingival tissue;
   (c) screwing the screw tip of the device by applying a pressure force on the screw tip towards the gingival tissue along a first axis while simultaneously applying a rotational force on the screw tip in a first direction causing the screw tip to enter the gingival tissue at the predetermined site and to enter cortical bone tissue underneath the predetermined site on the gingival tissue;
   (d) displacing cortical bone tissue radial to the first axis as a result of said screwing step;
   (e) stopping the screwing of the screw tip into the gingival tissue when the screw tip has reached a desired depth in the cortical bone tissue; and
   (f) removing the screw tip from the gingival tissue and the cortical bone tissue by applying a rotational force on the screw tip in a second direction opposite the first direction;
   wherein said displacing step does not cause removal of cortical bone tissue.

2. The method of claim 1, wherein the inflammatory response comprises an increased presence of cytokines near a tooth to be moved.

3. The method of claim 2, wherein the increased presence of cytokines promotes formation and activation of osteoclasts, which cause an increase in bone remodeling and movement.

4. The method of claim 1, further comprising repeating steps a)-f) a plurality of times at a different predetermined site each time.

5. The method of claim 1, wherein the predetermined site is proximal to a central or lateral tooth or in a palatal.

6. The method of claim 5, wherein the screw tip is about 3 mm in length.

7. The method of claim 1, predetermined site is near a malocclusion to be treated.

8. The method of claim 1, wherein the desired depth is less than 10 mm.

9. The method of claim 8, wherein the desired depth is about 3 mm, 5 mm, or 7 mm.

10. The method of claim 1, wherein the predetermined site is proximal to a posterior molar or in a mandible.

11. The method of claim 10, wherein the screw tip is about 7 mm in length.

12. The method of claim 1, wherein the screw tip is about 3 mm to 7 mm in length.

13. The method of claim 1, further comprising exerting a continuous force on the tooth to be moved.

14. The method of claim 13, wherein the exerting a continuous force is performed through the use of braces.

15. The method of claim 1, wherein contacting the screw tip of the device with gingival tissue at the predetermined site is performed at an about 90-degree angle.

16. A method of increasing movement of a tooth in a jaw by provoking an inflammatory response, the method comprising:
- (a) holding a handle of a device, the device having an elongate member extending from the handle, a screw tip at a distal end of the elongate member, and a sleeve configured to move along the elongate member to vary the length of exposed screw tip;
- (b) contacting the screw tip of the device with gingival tissue at a predetermined site on the gingival tissue;
- (c) screwing the screw tip of the device by applying a pressure force on the screw tip towards the gingival tissue along a first axis while simultaneously applying a rotational force on the screw tip in a first direction causing the screw tip to enter the gingival tissue at a predetermined site and to enter cortical bone tissue underneath the predetermined site on the gingival tissue;
- (d) displacing cortical bone tissue radial to the first axis as a result of said screwing step;
- (e) stopping the screwing of the screw tip when the sleeve makes contact with the gingival tissue; and
- (f) removing the screw tip from the gingival tissue and the cortical bone tissue by applying a rotational force on the screw tip in a second direction opposite to the first direction;

wherein said displacing step does not cause removal of cortical bone tissue.

17. The method of claim 16, wherein the sleeve is adjusted to a position along the elongated member thereby causing the length of exposed screw tip to be fixed.

18. The method of claim 17, wherein the length of exposed screw tip is about 3 mm, 5 mm or 7 mm.

19. The method of claim 16, wherein contacting the screw tip of the device with gingival tissue at the predetermined site is performed at an about 90-degree angle.

* * * * *